(12) United States Patent
Pardasani et al.

(10) Patent No.: US 12,094,611 B2
(45) Date of Patent: Sep. 17, 2024

(54) DEEP LEARNING BASED FETAL HEART RATE ANALYTICS

(71) Applicant: GE Precision Healthcare LLC, Milwaukee, WI (US)

(72) Inventors: Rohit Pardasani, Bengaluru (IN); Siddharth Ajith, Bengaluru (IN); John Michael Jordan, Severna Park, MD (US); Renee L Vitullo, Youngstown, OH (US)

(73) Assignee: GE Precision Healthcare LLC, Waukesha, WI (US)

( * ) Notice: Subject to any disclaimer, the term of this patent is extended or adjusted under 35 U.S.C. 154(b) by 213 days.

(21) Appl. No.: 17/517,251

(22) Filed: Nov. 2, 2021

(65) Prior Publication Data

US 2023/0136298 A1 May 4, 2023

(51) Int. Cl.
 *G16H 50/20* (2018.01)
 *A61B 5/00* (2006.01)
 *A61B 5/024* (2006.01)

(52) U.S. Cl.
 CPC ......... *G16H 50/20* (2018.01); *A61B 5/02411* (2013.01); *A61B 5/4356* (2013.01); *A61B 5/4362* (2013.01); *A61B 5/7267* (2013.01)

(58) Field of Classification Search
 CPC ..... G16H 10/00–80/00; A61B 5/02411; A61B 5/4356; A61B 5/4362; A61B 5/7267
 See application file for complete search history.

(56) References Cited

U.S. PATENT DOCUMENTS

| 9,439,597 B2 | 9/2016 | Warrick et al. |
| 9,805,164 B2 | 10/2017 | Hamilton |

(Continued)

FOREIGN PATENT DOCUMENTS

| CN | 104287711 A | 1/2015 |
| CN | 112971853 B | 8/2022 |
| IN | 202041014960 A | * 5/2020 |

(Continued)

OTHER PUBLICATIONS

Gao et al., "Fetal Heart Baseline Extraction And Classification based on Deep Learning," 2019 International Conference on Information Technology and Computer Application (ITCA). (Year: 2019).*

(Continued)

*Primary Examiner* — Jonathon A. Szumny
(74) *Attorney, Agent, or Firm* — Amin, Turocy & Watson, LLP

(57) ABSTRACT

Techniques are described for performing fetal heart rate (FHR) analytics using machine learning techniques. According to an embodiment, computer-implemented method comprises training a machine learning model using a supervised machine learning process to identify patterns in training cardiotocograph data that correspond to defined physiological events associated with respective fetuses and mothers of the fetuses represented in the training cardiotocograph data. The method further comprises receiving new cardiotocograph data for a fetus and mother in real-time over a period of labor and applying the machine learning model to the new cardiotocograph data as it is received to identify the patterns in the new cardiotocograph data.

19 Claims, 10 Drawing Sheets

(56) References Cited

U.S. PATENT DOCUMENTS

| | | | |
|---|---|---|---|
| 2020/0214679 A1* | 7/2020 | Silberman | A61B 8/465 |
| 2021/0015375 A1* | 1/2021 | Kim | A61B 5/4362 |

FOREIGN PATENT DOCUMENTS

| | | | |
|---|---|---|---|
| RU | 2754723 C1 * | 9/2021 | |
| WO | 2019190208 A1 | 10/2019 | |
| WO | WO-2020120345 A1 * | 6/2020 | |

OTHER PUBLICATIONS

Dr. C Sundar, "Fertility Care Management System using ANN based Machine Learning Techniques," Advances in Natural and Applied Sciences. 10(2); pp. 160-169. (Year: 2016).*

Pradhan et al., "A Machine Learning Approach for the Prediction of Fetal Health using CTG," 2021 19th OITS International Conference on Information Technology (OCIT). (Year: 2021).*

Sundar et al., "Classification of Cardiotocogram Data using Neural Network based Machine Learning Technique," International Journal of Computer Applications (0975-888); vol. 47-No. 14, Jun. 2012. (Year: 2012).*

Alsaggaf et al., "Predicting fetal hypoxia using common spatial pattern and machine learning from cardiotocography signals," Applied Acoustics 167 (2020) 107429; https://doi.org/10.1016/j.apacoust.2020.107429. (Year: 2020).*

Fergus et al., "Prediction of Intrapartum Hypoxia from Cardiotocography Data Using Machine Learning," Applied Computing in Medicine and Health. http://dx.doi.org/10.1016/B978-0-12-803468-2.00006-0 (Year: 2016).*

Hoodbhoy et al., "Use of Machine Learning Algorithms for Prediction of Fetal Risk using Cardiotocographic Data," © 2019 International Journal of Applied and Basic Medical Research | Published by Wolters Kluwer—Medknow; DOI: 10.4103/ijabmr.IJABMR_370_18 (Year: 2019).*

Amin et al., "Classifying Cardiotocography Data based on Rough Neural Network," (IJACSA) International Journal of Advanced Computer Science and Applications, vol. 10, No. 8, 2019. (Year: 2019).*

Miao et al., "Cardiotocographic Diagnosis of Fetal Health based on Multiclass Morphologic Pattern Predictions using Deep Learning Classification," (IJACSA) International Journal of Advanced Computer Science and Applications, vol. 9, No. 5, 2018. (Year: 2018).*

Ogasawara et al., "Deep neural network-based classification of cardiotocograms outperformed conventional algorithms," Scientific Reports | (2021) 11:13367 | https://doi.org/10.1038/s41598-021-92805-9. (Year: 2021).*

CN 112971853A, Machine Translation; 18 pages.

EP application 22203798.8 filed Oct. 26, 2022—extended Search Report issued Mar. 15, 2023; 13 pages.

Frasch M G et al: "Detection of preventable fetal distress during labor from scanned cardiotocogram tracings using deep learning", arxiv.org, Cornell University Library, 201 Olin Library Cornell University Ithaca, NY 14853, Jun. 1, 2021 (Jun. 1, 2021), XP081982225.

Haweel M T et al: "Polynomial FLANN Classifier for Fetal Cardiotocography Monitoring", 2021 38th National Radio Science Conference (NRSC), IEEE, vol. 1, Jul. 27, 2021 (Jul. 27, 2021), pp. 262-270, XP033959744, DOI:10.1109/NRSC52299.2021.9509832 [retrieved on Aug. 9, 2021].

O'sullivan M et al: "Classification of fetal compromise during labour: signal processing and feature engineering of the cardiotocograph", 2021 29th European Signal Processing Conference (EUSIPCO), EURASIP, Aug. 23, 2021 (Aug. 23, 2021), pp. 1331-1335, XP034038435, DOI: 10.23919/EUSIPCO54536.2021.9616289 [retrieved on Nov. 15, 2021].

Zhao, Z. et al. | DeepFHR: intelligent prediction of fetal Acidemia using fetal heart rate signals based on convolutional neural network. BMC Med Inform Decis Mak. Dec. 30, 2019;19(1):286. doi: 10.1186/s12911-019-1007-5. PMID: 31888592; PMCID: PMC6937790, 15 pages.

Feng, G. et al. | Supervised and Unsupervised Learning of Fetal Heart Rate Tracings with Deep Gaussian Processes. 2018 14th Symposium on Neural Networks and Applications (NEUREL), 2018, pp. 1-6, doi: 10.1109/NEUREL.2018.8586992, 6 pages.

Fotiadou, E. et al. | Deep Convolutional Long Short-Term Memory Network for Fetal Heart Rate Extraction. 2020 42nd Annual International Conference of the IEEE Engineering in Medicine & Biology Society (EMBC), 2020, pp. 1-4, doi: 10.1109/EMBC44109.2020.9175442, 4 pages.

Liang, Sai et al. | Automatic Evaluation of Fetal Heart Rate Based on Deep Learning. 2021 2nd Information Communication Technologies Conference (ICTC), 2021, pp. 235-240, doi: 10.1109/ICTC51749.2021.9441583, 6 pages.

* cited by examiner

DEEP LEARNING BASED FETAL HEART RATE ANALYTICS

TECHNICAL FIELD

This application relates to a deep learning-based approach for fetal heart rate (FHR) analytics.

BACKGROUND

Cardiotocography (CTG) is widely used in pregnancy as a method of assessing fetal well-being, particularly during labor and delivery. CTG records changes in the fetal heart rate (FHR) and their temporal relationship to uterine contractions. The machine used to perform the monitoring is called a cardiotocograph, more commonly known as an electronic fetal monitor (EFM). Simultaneous recordings are performed by two separate transducers, one for the measurement of the FHR and a second one for the uterine contractions, also referred to as the uterine activity (UA). The transducers may be either external or internal. The cardiograph recordings are typically in the form of graphical tracings that are either printed on a continuous strip of paper and/or displayed on a graphical display monitor.

The FHR and UA tracings are typically analyzed manually by the obstetric medical team (e.g., including nurses, resident physicians, nurse midwives, attending physicians, etc.) over the course of labor to identify abnormal patterns. The identification of the patterns helps in assessing various parameters and/or conditions associated with the fetus and/or the mother, such as baseline FHR, contraction duration and frequency, contraction nature (e.g., late, early, variably), FHR variability, and presence of tachysystole. Assessment of these parameters/conditions plays a vital role in identifying fetal abnormalities and the need for intervention during labor.

Presently there are multiple challenges in analysis of FHR-UA tracings. The manual visual assessment of the graphical tracings requires expertise and may be biased due to the level of experience of the physician/nurse performing the analysis. Although some automated methods for assessing FHR-UA tracings have been developed, these methods are based solely on guidelines and definitions for identifying patterns and conditions expressed in terms of mathematical rules. The existing computational/algorithmic methods of assessment are thus strictly statistical, and rule based. This automatic assessment is often not in accordance with the analysis based on experience of clinicians. Most experts feel that going strictly by these rule-based definitions is not appropriate in real life scenarios. Thus, there is a need for a computational method for analysis of FHR-UA tracings which is not solely rule-based and assimilates the visual assessment expertise of clinicians in real-life scenarios.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments herein, systems, computer-implemented methods, apparatus and/or computer program products are described that provide a deep learning-based approach for fetal heart rate analytics. The disclosed artificial intelligence (AI) based approach involves a deep learning model trained on annotated data to analyze the FHR-UA strips. This data driven approach ensures that the contextual clinical understanding will be accurately captured during inferencing due to the model being trained using FHR-UA strip data annotated by experts as the ground truth.

According to an embodiment, a system is provided that comprises a memory that stores computer executable components, and a processor that executes the computer executable components stored in the memory. The computer executable components comprise a training component that trains a machine learning model using a supervised machine learning process to identify patterns in training cardiotocograph data that correspond to defined physiological events associated with respective fetuses and mothers of the fetuses represented in the training cardiotocograph data. The computer executable components further comprise a monitoring component that receives new cardiotocograph data for a fetus and mother in real-time over a period of labor, and an inferencing component that applies the machine learning model to the new cardiotocograph data as it is received to identify the patterns in the new cardiotocograph data.

In accordance with this this system, at least some of the training cardiotocograph data comprises annotated cardiotocography data annotated with information identifying the patterns and the defined physiological events that respectively correspond to the patterns, wherein the supervised machine learning process comprises employing the annotated cardiotocograph data as ground truth. In some implementations, the annotated cardiotocograph data comprises annotations applied to graphical cardiotocograph strips generated from the training cardiotocograph data. The computer executable components may further comprise a pre-processing component that converts the annotated cardiotocograph data into a machine-readable format for processing by the machine learning model.

In one or more embodiments, the computer executable components further comprise an analysis component that determines occurrence of the defined physiological events based on the patterns in the new cardiotocograph data, and a reporting component that provides event information regarding the occurrence of the defined physiological events to one or more clinicians via one or more output devices over the period of labor. For example, the defined physiological events may include, but are not limited to, a FHR acceleration, a FHR deceleration, a uterine contraction, a period of FHR variability, and a uterine tachysystole. In some implementations, the analysis component further determines parameters associated with the defined physiological events based on the new cardiotocograph data and the patterns in the new cardiotocograph data, and the reporting component further provides parameter information regarding the parameters associated with the defined physiological events with the event information. For example, the parameters may include, but are not limited to: baseline FHR, timing of FHR acceleration, duration of FHR acceleration, degree of FHR acceleration, type of FHR acceleration, timing of FHR rate deceleration, duration of FHR deceleration, degree of FHR deceleration, type of FHR rate deceleration, timing of FHR rate period of variability, duration of FHR period of variability, degree of FHR variability, contraction timing, contraction duration, contraction frequency, and contraction type.

In some implementations, the computer executable components further comprise a feedback component that facilitates receiving feedback information from the one or more clinicians regarding accuracy of the event information and the parameter information, and a logging component that logs the feedback information with the new cardiograph data in an indexed data structure, wherein the training component further employs the feedback information in association with retraining and refining the machine learning model.

In some embodiments, elements described in the disclosed systems and methods can be embodied in different forms such as a computer-implemented method, a computer program product, or another form.

DETAILED DESCRIPTION

Figure 1:
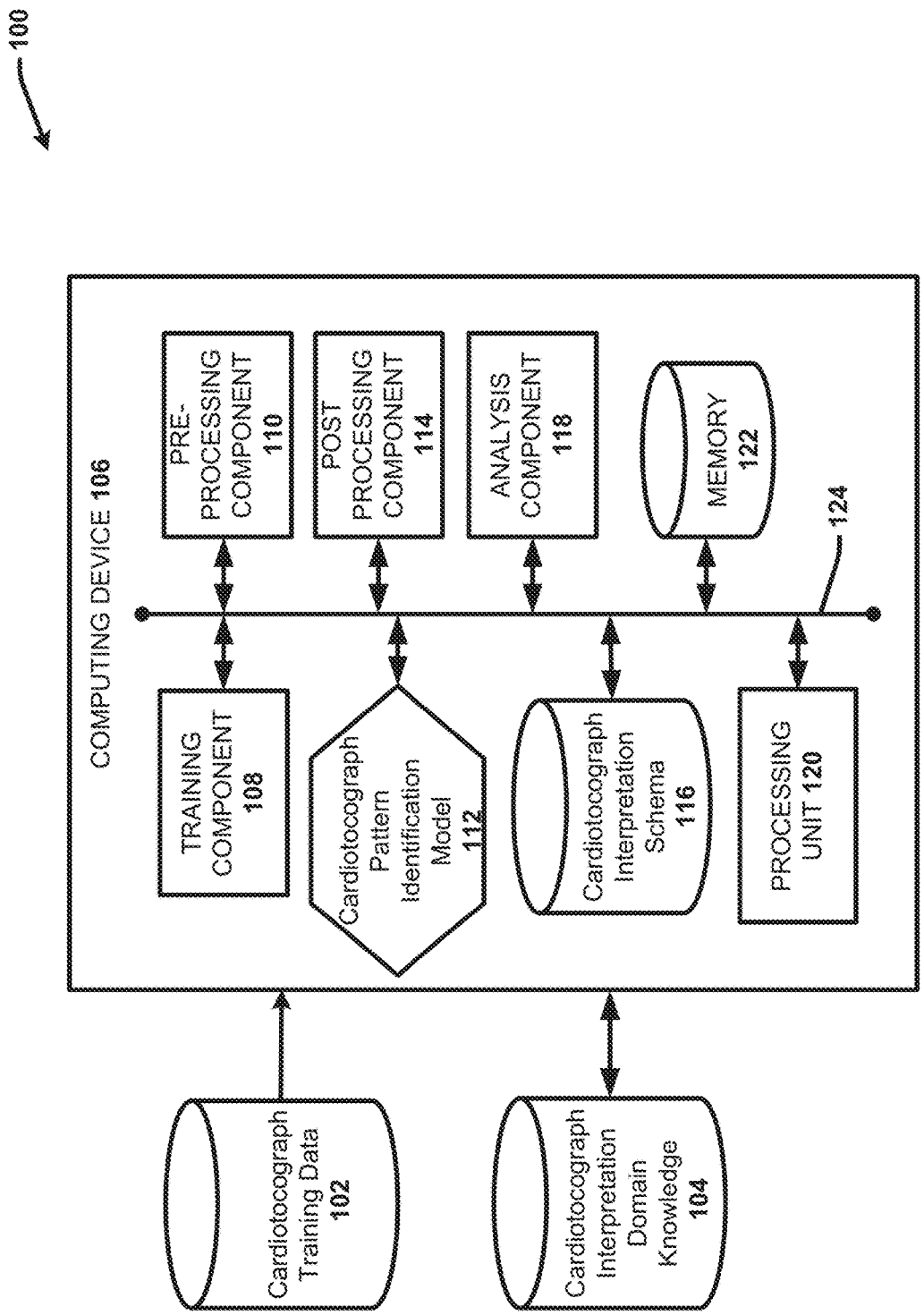
FIG. 1 illustrates an example system that facilitates FHR analytics using machine learning techniques in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to systems, computer-implemented methods, apparatus and/or computer program products that facilitate automated interpretation and analysis of patient cardiotocograph data in real-time, particularly in the context of labor and delivery. The disclosed techniques solve the challenge of automatic analysis of FHR and UA tracings using a data driven approach rooted in machine learning as opposed to a solely rule-based approach. This data driven approach involves training one or more machine learning models using a supervised machine learning process to identify distinct patterns in cardiotocograph data that correspond to defined physiological events associated with the fetus and/or the mother. For example, the defined physiological events can include, but are not limited to, a FHR acceleration, a FHR deceleration, a period of FHR variability and a contraction. Once trained, the one or more pattern recognition models can be deployed in real-life settings in inferencing mode to automatically detect occurrence of the defined physiological events based on cardiograph data captured for a mother and fetus in real-time. The training data used to train the one or more pattern recognition models includes cardiograph data annotated with information identifying the patterns and their corresponding physiological events. The subjects represented in the training data can include a plurality of different mothers and their fetuses as monitored over their course of labor. This data driven approach ensures that the inferences generated by the pattern recognition models are based on learning from analysis of actual cardiograph data captured for real patients, and thus mimics the visual FHR-UA strip analysis of experts in actual clinical contexts.

In various embodiments, the one or more trained cardiotocograph pattern recognition models can be integrated into software and/or hardware products that involve FHR monitoring and diagnosis. The trained models can be used to evaluate both static and streaming cardiotocograph data. For example, the one or more models can be used to retrospectively analyze recorded cardiograph data captured for a subject (e.g., mother and fetus) during a monitoring session. The one or more models can also be used to analyze a continuous stream of cardiotocograph data flowing from a cardiotocograph device attached to a mother and fetus in real-time. Regardless of the deployment scenario, the trained cardiotocograph pattern recognition model will drastically reduce the manual strip assessment time while minimizing errors.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 presents an example system 100 that facilitates FHR analytics using machine learning techniques in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

In this regard, system 100 comprises a computing device 106 that includes several computer executable components. These computer executable components include training component 108, pre-processing component 110, cardiotocograph pattern identification model 112, post processing component 114, and analysis component 118. These computer/machine executable components (and other described herein) can be stored in memory associated with the one or more machines (e.g., computing device 106). The type of the computing device 106 can vary. For example, the computing device 106 can correspond to a personal computing device (e.g., a desktop computer, a laptop computer, a smartphone, etc.), a server device, a mobile device, a virtual device, and so on. The memory can further be operatively coupled to at least one processor, such that the components can be executed by the at least one processor to perform the operations described. For example, in some embodiments, these computer/machine executable components can be stored in memory 122 which can be coupled to processing unit 120 for execution thereof. Examples of said and memory and processor/processing unit as well as other suitable computer or computing-based elements, can be found with reference to FIG. 10, and can be used in connection with implementing one or more of the systems or components shown and described in connection with FIG. 1 or other figures disclosed herein. The computing device 106 further includes a device bus 124 that communicatively and operatively couples the various components and elements of the computing device 106 to one another.

System 100 further includes various data structures (e.g., data stores, databases, data files, and the like) that provide information used by the computer-executable components illustrated in FIG. 1 (and other figures described herein). This information includes cardiotocograph training data 102, cardiotocograph interpretation domain knowledge 104 and cardiotocograph interpretation schema 116. The type of data structures and/or data sources in which this information is stored and located can vary. The computing device 106 and/or one or more components of the computing device 106 can be operatively and communicatively coupled to these data structures either directly or via one or more wired or wireless communication networks (e.g., the Internet, an Intranet, etc.).

The training component 108 provides for training and developing one or more machine learning models to identify one or more distinct patterns in cardiotocograph data that correspond to one or more defined physiological events associated with the fetus and/or mother from which the cardiotocograph data was captured. In the embodiment shown, these one or more machine learning models correspond to cardiotocograph pattern identification model 112. Although a single model is shown, it should be appreciated that the number of cardiotocograph pattern identification models 112 can vary. For example, in some implementations, the training component 108 can train a single model to identify different patterns corresponding to different physiological events. In other implementations, the training component 108 can train separate models to identify different patterns corresponding to different physiological events. In other implementations, the training component 108 can train separate models for different types of patients and/or patient groups. For example, the different types of patients or patient groups can be defined based on attributes associated with the mother and/or the fetus, including demographic attributes (e.g., age, gender body mass index (BMI), height/weight, location), clinical factors (e.g., comorbidities, risk level, pathology, etc.), medical history factors (e.g., maternal medical illness, obstetric complications, etc.), psychosocial risk factors (e.g., no prenatal care), and so one. Still in other implementations, the training component 108 can train separate models tailored to different types of cardiotocograph monitoring devices (e.g., internal verses external, different device makes/models, etc.).

The type of machine learning model architecture used for the cardiotocograph pattern identification model 112 can vary. For example, the cardiotocograph pattern identification model 112 can employ various types of machine algorithms, including (but not limited to): deep learning models, neural network models, deep neural network models (DNNs), convolutional neural network models (CNNs), generative adversarial neural network models (GANs), long short-term memory models (LSTMs), attention-based models, transformers, or a combination thereof. In some embodiments, the cardiotocograph pattern identification model 112 can additionally or alternatively employ a statistical-based model, a structural based model, a template matching model, a fuzzy model or a hybrid, a nearest neighbor model, a naïve Bayes model, a decision tree model, a linear regression model, a k-means clustering model, an association rules model, a q-learning model, a temporal difference model, or a combination thereof.

Regardless of the specific type of machine learning model architecture used, the training component 108 employs a data-driven supervised machine learning process to train and develop the one or more cardiotocograph pattern identification models 112. In a supervised learning framework, the learning system is first given examples of data by which human experts or annotators apply classification labels to a corpus of data. The class labels are then used by the learning algorithm to adapt and change it's internal, mathematical representation (such as the behavior of artificial neural networks) of the data and mapping to some predication of classification etc. The training consists of iterative methods using numerical, optimization techniques that reduce the error between the desired class label and the algorithm's prediction. The newly trained model is then given new data as an input and, if trained well, can classify or otherwise provide assessment of novel data.

In this regard, the training data used to train the one or more cardiotocograph pattern identification models 112 includes at least some labeled cardiotocograph data annotated with information identifying known patterns and their corresponding physiological events. In the embodiment shown, this training data is represented as cardiotocograph training data 102. The cardiotocograph training data 102 can include previously recorded cardiotocograph data captured for a plurality of different mothers and their respective unborn fetuses over a duration of time. In various embodiments, the duration of time includes the duration of labor, such as from the onset of labor to delivery, or a portion of time there between. Additionally, or alternatively, the cardiotocograph training data 102 may include cardiotocograph data recorded for subjects (e.g., respective mothers and their unborn fetuses) at any point during their pregnancy, such as that recorded in association with a monitoring/check-up session.

In one or more embodiments, the cardiotocograph training data 102 for each subject (e.g., each mother and fetus combination) includes both FHR tracing data and UA tracing data captured simultaneously, referred to herein as FHA-UA tracing data. The FHR tracing data includes information that tracks the FHR over time, while the UA tracing data includes information that tracks the UA over time. The frequency of sampling of the FHR measurements and the UA measurements can vary depending on the type of cardiotocograph device used. For example, the sampling frequency may be every millisecond, every second, every few seconds, every 10 seconds, and so on. In accordance with conventional FHR monitoring systems, the FHR and UA recordings are typically in the form of graphical tracings that are either printed on a continuous strip of paper and/or displayed on a graphical display monitor. The simultaneous recordings of the FHR and the UA are typically performed by two separate transducers, one for the measurement of the FHR and a second one the UA. The transducers may be either external or internal.

Figure 2:
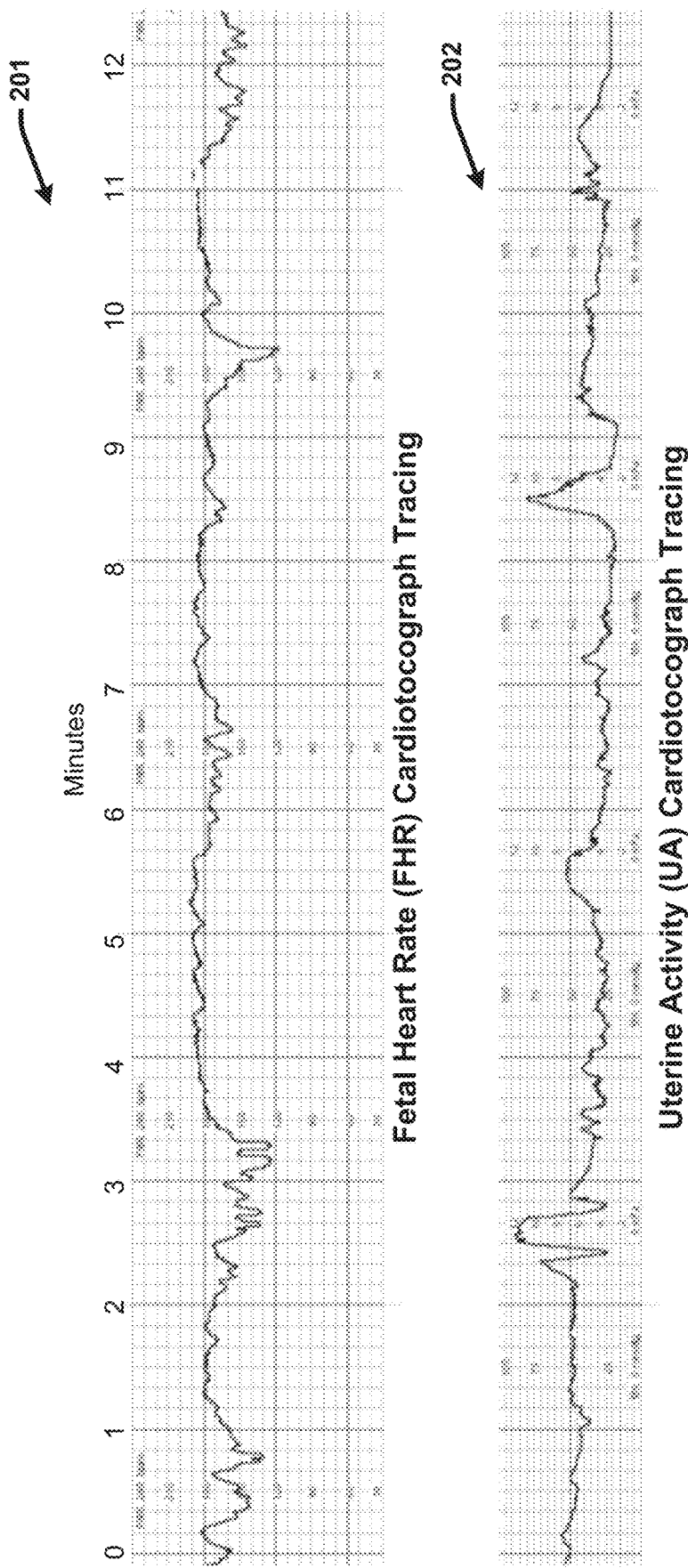
FIG. 2 presents example FHR and UA tracings in accordance with one or more embodiments of the disclosed subject matter.

FIG. 2 presents example FHR and UA tracings in accordance with one or more embodiments of the disclosed subject matter. Tracing 201 correspond to an FHR tracing for an unborn fetus and tracing 202 corresponds to a simultaneously recorded UA tracing for the mother of the unborn fetus. The FHR tracing 201 plots the heart rate of the fetus over time while the UA tracing plots the mother's UA over time (e.g., measure in minutes).

FHR and UA tracings such as those depicted in FIG. 2 are typically visually analyzed manually by nurses, resident physicians, nurse midwives and attending physicians over the course of labor to identify abnormal patterns. These patterns can include patterns in the FHR tracing alone, the UA tracing alone, as well as combined patterns in the simultaneous recordings. The identification of the patterns helps in assessing various parameters and/or conditions associated with the fetus and/or the mother, such as baseline FHR, contraction duration and frequency, contraction nature (e.g., late, early, variably), FHR variability, and presence of tachysystole. Assessment of these parameters/conditions plays a vital role in identifying fetal abnormalities and the need for intervention during labor.

For example, obstetric clinicians are trained to visually examine the FHR-UA tracings identify distinct patterns in the graphical representations that have been known to correspond to defined physiological events associated with the fetus and/or the mother. Guidelines defining the distinct patterns and the physiological events/conditions associated with them have been defined in medical literature. For example, individual uterine contractions are seen as peaks on the UA tracing 202. The guidelines for evaluating contraction patterns from a UA tracing such as tracing 201 generally involve identifying the frequency of the peaks/contractions (e.g., number of contractions per defined time interval), the duration of the contractions, and the intensity of the contractions. In another example, FHR accelerations are seen as abrupt peaks on the FHR tracing 201 while FHR decelerations are seen as abrupt valleys or spikes. The guidelines for evaluating FHR tracing data are generally based on identifying and evaluating the degree of variability in the graphical representation (e.g., number of peaks and valleys, frequency of peaks and valleys, amplitude of the peaks and valleys, etc.), identifying and evaluating peaks and valleys corresponding to accelerations and decelerations, and correlating the peaks and valleys in the FHR tracing with contraction peaks. Trained clinicians can extract these parameters from the UA tracing visually by examining the patterns in the graphical representation of the data.

With reference to FIGS. 1 and 2, the disclosed techniques automate this visual/manual abnormal pattern identification process be training the one or more cardiotocograph pattern identification models 112 to identify the abnormal patterns and/or other defined patterns in the cardiotocograph data that correspond to defined physiological events associated with the fetus and/or the mother. For example, the defined physiological events may include, but are not limited to, a FHR acceleration, a FHR deceleration, a period of FHR variability, and a uterine contraction. Various other physiological events associated with the fetus and/or mother that may also be correlated to distinct patterns in the cardiotocograph data are also envisioned. For example, some other physiological events that may be represented by defined patterns in the FHR-UA data can include but are not limited to: fetal tachycardia, fetal bradycardia, saltatory variability, variable decelerations, late decelerations, persistent late decelerations with loss of beat-to-beat variability, non-reassuring variable decelerations associated with loss of beat-to-beat variability, prolonged severe bradycardia, and sinusoidal pattern. The number of different patterns and correlated physiological events can vary.

As noted above, to facilitate this end, the training component 108 trains the cardiograph pattern identification models 112 to identify the defined patterns in cardiotocograph data corresponding to the defined physiological events using a supervised learning processes that involves training the model 112 to learn from labeled cardiotocograph training data 102. In this regard, at least some of the cardiotocograph training data 102 includes annotation information applied thereto (or otherwise associated therewith) that identifies one or more patterns in the cardiograph data (e.g., FHR-UA tracing data) and their corresponding physiological events or conditions. The number of different patterns and correlated physiological events can vary. In some embodiments, the annotated cardiotocograph data can include marked-up FHR-UA tracings with annotation marks applied directly to the graphical tracings, as illustrated in FIGS. 3 and 4.

Figure 3:
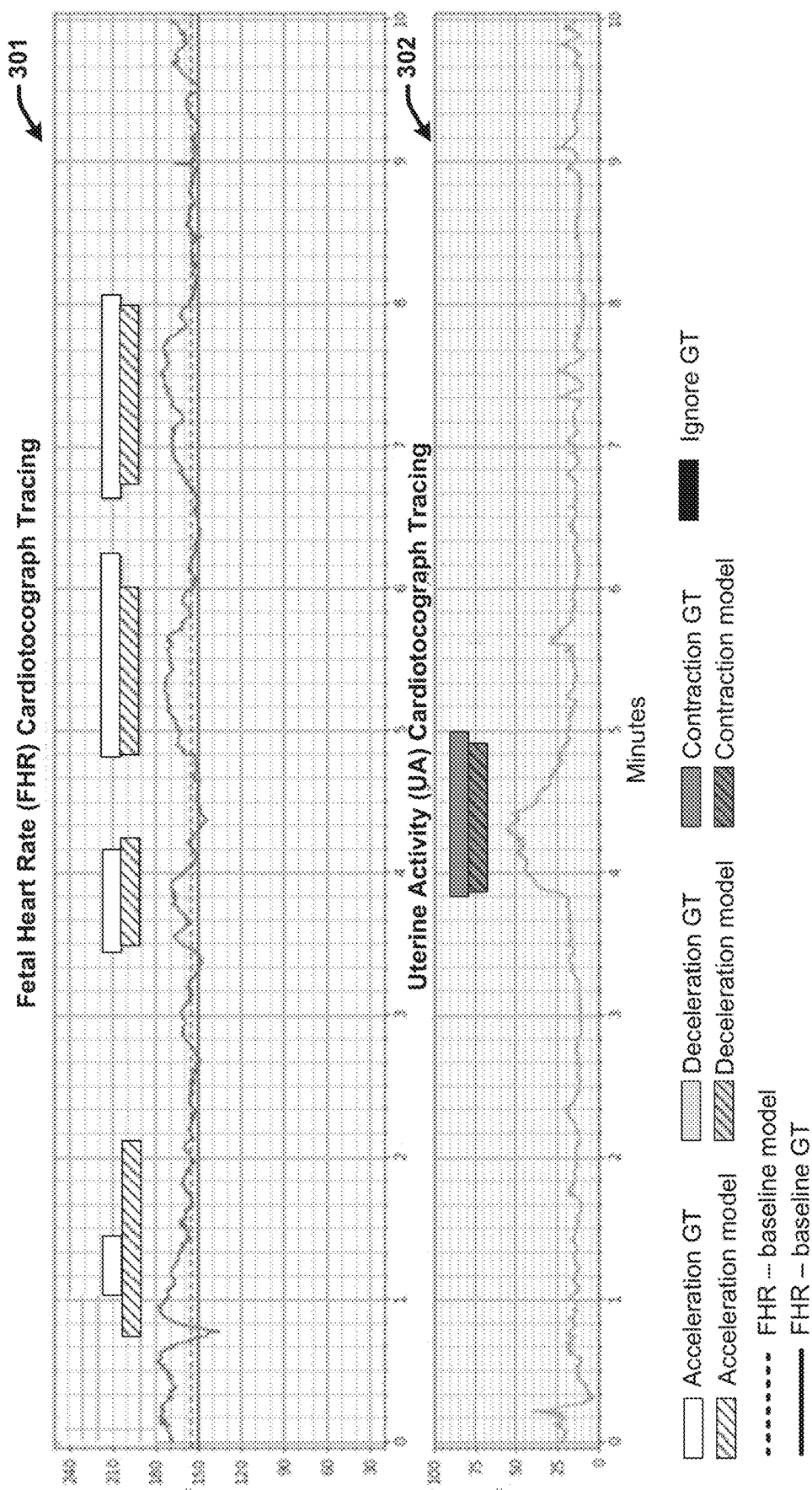
FIG. 3 presents example FHR and UA tracings comparing the model identified patterns with the ground truth annotated patterns in accordance with one or more embodiments of the disclosed subject matter.
Figure 4:
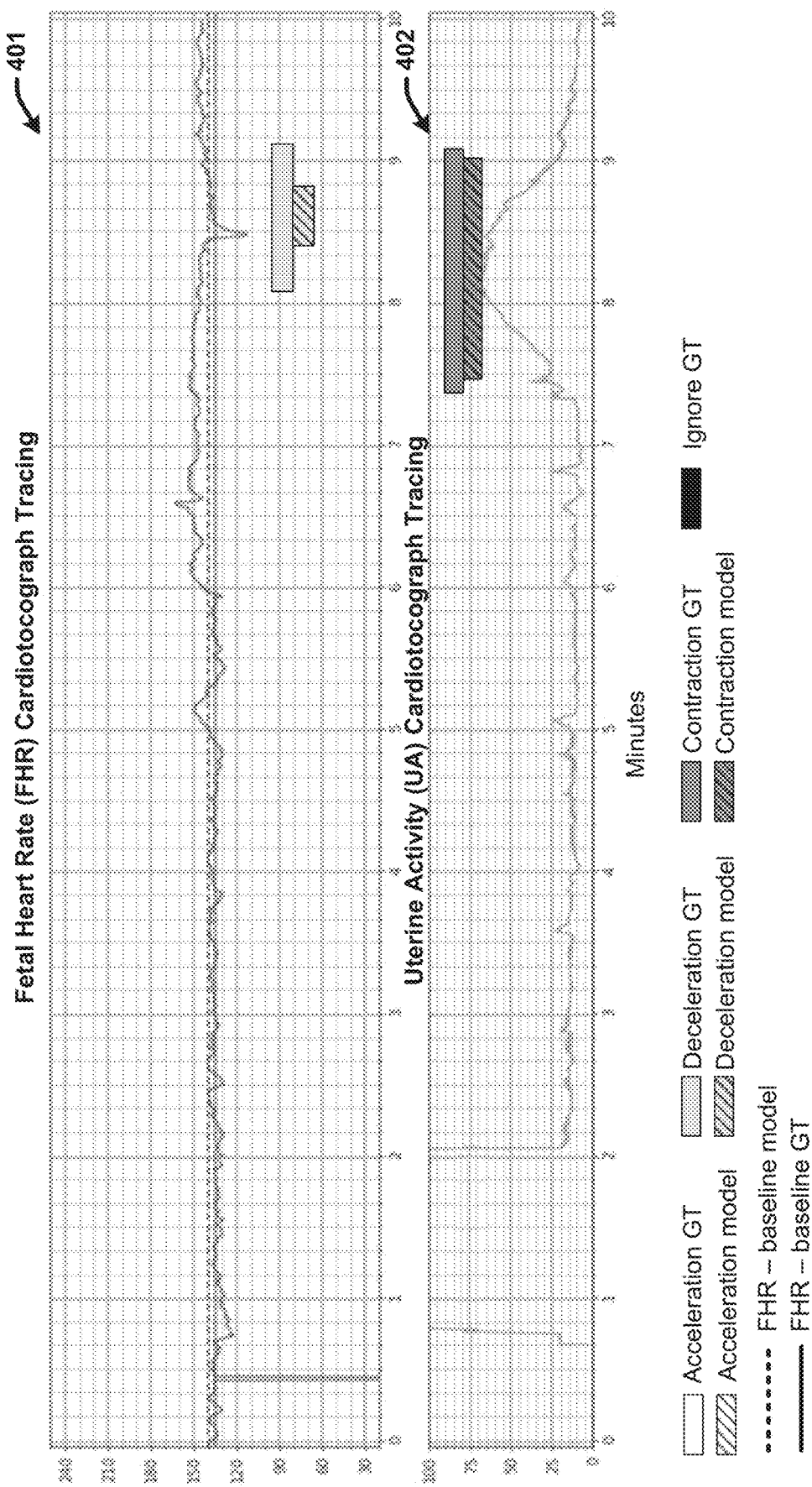
FIG. 4 presents additional example FHR and UA tracings comparing the model identified patterns with the ground truth annotated patterns in accordance with one or more embodiments of the disclosed subject matter.

In this regard, FIGS. 3 and 4 present example FHR and UA tracings comparing the model identified patterns with the ground truth annotated patterns in accordance with one or more embodiments of the disclosed subject matter. Tracings 301 and 401 correspond to FHR tracings and tracking 302 and 3402 correspond to the UA tracings. In accordance with these examples, each set of tracings (e.g., tracings 301 and 302 corresponding to one set and tracings 401 and 402 corresponding to another set) represent a 10-minute window of time. As described in greater detail below, in some embodiments, the cardiotocograph pattern identification model 112 can be trained to identify patterns in input data samples that consist of FHR-UA tracing data tracked for a defined window of time, such as 10 minutes or another timeframe (e.g., each input sample can represent a 10-minute window). The respective tracings are marked with graphical markings in the form of horizontal bars over (or otherwise in alignment with) the distinct patterns in the tracing data that correspond to defined physiological events. In these examples, the physiological events include a FHR acceleration, a FHR deceleration and a contraction. In both FIGS. 3 and 4, the upper bars with solid fill (e.g., without the slanted lines) correspond to the manually annotated ground truth, while the lower bars with the slanted lines correspond to the patterns automatically identified by a trained version of the cardiotocograph pattern identification model 112. The manually annotated ground truth can also include manually identified regions/patterns in the cardiotocograph data that an expert understands as not corresponding to any defined physiological event or condition yet may assumes could potentially be misinterpreted by the model during training (e.g., due to a tendency for manual reviewers to misinterpret these types of patterns). By annotating these "ignore" regions, the accuracy of the model can be further enhanced to minimize false positive detections.

With reference again to FIG. 1, the format of the training cardiotocograph data 102, including the annotated cardiotocograph data (and any unannotated samples if included), can vary. In some embodiments, the format of the cardiotocograph training data 102 can include digital graphical FHR-UA tracings that correspond to those depicted in FIGS. 2-4. With these embodiments, the digital graphical FHR-UA tracings may be annotated with manually applied mark-up data in the manner shown in FIGS. 2-4 and/or in a similar manner. Additionally, or alternatively, the cardiotocograph training data 102 can include the raw signal or waveform data used to generate the digital graphical FHR-UA tracings. For example, the raw signal data for the FHR information can include FHR measurements recorded as a function of time with corresponding time stamps for each measurement. Likewise, the raw signal data for the UA information can include UA measurements recorded as a function of time with corresponding time stamps for each measurement.

The format of cardiotocograph data supplied as input to the cardiotocograph pattern identification model 112 (e.g., during inferencing and/or training) may be the same as that of the cardiotocograph training data 102 or optionally transformed into a different machine-readable format by the pre-processing component 110. For example, in some embodiments in which the cardiotocograph training data 102 is received as a digital graphical FHR-UA tracing, the pre-processing component 110 may convert the digital graphical FHR-UA tracing data into its corresponding raw signal data prior to input into the cardiotocograph pattern identification model 112. The pre-processing component 110 can further translate the manually applied ground truth annotation data from the annotated digital graphical FHR-UA tracings to their corresponding raw signal data segments. Likewise, in some embodiments in which cardiotocograph training data 102 is received as raw signal data, the pre-processing component 110 may convert the raw signal data into a corresponding digital graphical FHR-UA tracing prior to input into the cardiotocograph pattern identification model 112.

As noted above, in some embodiments, the training component 108 can train the cardiotocograph pattern identification model 112 to identify distinct patterns in input FHR-UA tracing data samples that represent a window of time, such as 10 minutes or another time interval. In some implementations of these embodiments, the pre-processing component 108 can generate these input data samples prior to processing by the model 112 by cutting/splicing a continuous FHR-UA tracing for a same subject (e.g., same mother/fetus combination) into sequential segments, wherein each segment represents a defined window of time (e.g., each segment corresponds a 10-minute window of FHR-UA strip data). The pre-processing component 110 can also perform other data pre-processing functions to pre-process the input data prior to input to the model 112 (e.g., during training and/or inferencing). For example, the pre-processing component 110 can pre-process the input data to fill outliers and missing values (e.g., a process known as data cleansing or data engineering). The training component 108 can further employ a supervised machine learning process to train the cardiotocograph pattern identification model 112 to identify the distinct patterns in the input data samples that correspond to defined physiological events (e.g., a FHR acceleration, a FHR deceleration, a period of FHR variability, a contraction, etc.) using the manually annotated ground truth data associated with at least some of the input data samples, as described with reference to FIG. 5.

Figure 5:
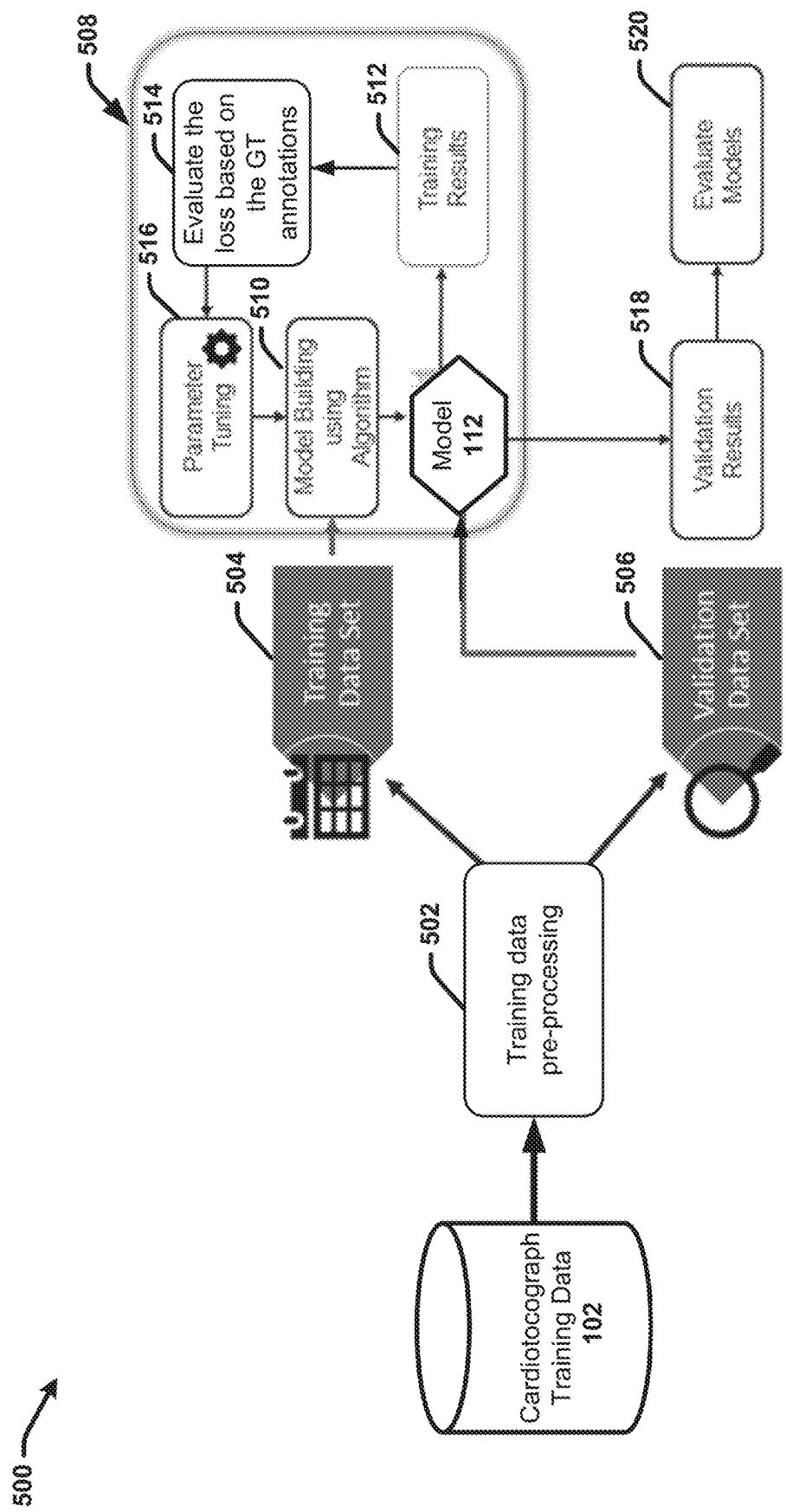
FIG. 5 presents an example training process for training a machine learning model to detect defined patterns in cardiograph data in accordance with one or more embodiments of the disclosed subject matter.

In this regard, FIG. 5 presents an example training process 500 for training a machine learning model to detect defined patterns in cardiograph data in accordance with one or more embodiments of the disclosed subject matter. In various embodiments, the pre-processing component 110 and the training component 108 can apply process 500 to develop and train the one or more cardiotocograph pattern identification models 112. Repetitive description of like elements employed in respective embodiments is omitted for sake of brevity.

The training process 500 can initially involve pre-processing the cardiotocograph training data 102 by the pre-processing component 110 at 502. The specific pre-processing steps that are performed at 502 can vary. For example, in some embodiments, the pre-processing component 110 can be configured to segment any continuous strips of FHR-UA data for a same subject into separate input samples that represent short windows of time (e.g., 10 minutes or the like). In other implementations, the cardiotocograph training data 102 may already formatted as separate input data samples corresponding to defined durations of time (e.g., 10 minutes or the like). The pre-processing at 502 can also involve converting the cardiotocograph training data 102 from one format to another machine-readable format for processing by the model 112 (e.g., from signal data to graphical FHR-UA tracing data, or vice versa). The pre-processing at 502 can also involve data cleansing/engineering to fill outliers and/or missing values.

Once pre-processed, the training component 108 can divide the cardiotocograph training data 102 into a training data set 504 and a validation data set 506. The training data set 504 is used to train and build the model 112 in accordance with process 508. Process 508 involves model building at 510, which involves applying the input data samples included in the training data set 504 to the model 112 to generate training results 512. The training results 512 or model output can include information that identifies any distinct patterns in each input data sample (e.g., or no pattern if one is not identified), that correspond to one or more defined physiological events (e.g., a FHR acceleration, a FHR deceleration, a region of marked variability, and/or a contraction), information classifying the specific physiological event corresponding to each pattern, and/or information describing/defining attributes or parameters of the identified pattern. For example, the information describing/defining the attributes or parameters of an identified pattern can include information identifying the specific portions of the data in which the one or more patterns are encompassed (e.g., the FHR data, the UA data, or a combination thereof), the start and stop time points of the one or more patterns, and/or the distribution of measurement values that constitute the pattern (e.g., the specific FHR measurements, the specific UA measurements, and/or the combinations thereof). The format of the model output data can vary. For example, the output data can be formatted in a machine-readable format, in a human readable format, as a graphical FHR-UA tracing with model applied annotation mark ups (e.g., as shown in FIGS. 3 and 4), as text, or another format.

At 514, process 508 involves evaluating the loss based on the ground truth (GT) annotations applied to the corresponding input data samples. The type of loss function employed by the training component 108 can vary. For example, the loss function may be based on mean squared error, cross-entropy, hinge loss, and KL divergence, a distance metric or the like. The loss function evaluation at 514 generally involves determining a measure of difference in accuracy between the training results 512 and the actual ground truth provided by clinical experts. In accordance with the subject training, the training results 512 can define a pattern identified in a training sample by various metrics that represents the distinct timing and value measurements (e.g., FHR values and/or UA values) that make up the distinct pattern. For example, the pattern can be represented as a graphical distribution of points in space, a reduced dimensionality feature vector, a geometrical shape, a value matrix, or the like. Regardless of the manner in which the pattern is represented/defined, the loss evaluation at 514 involves determining differences between the representation of the pattern in the training results and the ground truth representation for the pattern (or no pattern if ground truth indicates no pattern should have been identified).

For example, in some implementations, training component 108 can perform the loss evaluation at 514, by computing a similarity score between an identified pattern and the corresponding ground truth pattern and determine the degree of loss based on the match similarity score. The training component 108 can compute the similarity score using one or more statistical techniques, and/or one or more artificial intelligence techniques. Additionally, or alternatively, the training component 108 can compute the similarity score based on a distance metric, such as a Hamming distance, a Jaccard distance/Index, a Dice score/coefficient, or the like.

At 516, process 508 further comprises adjusting the model weights and/or parameters based on the loss to reduce the amount of loss on the next evaluation of the next training data sample. This processes 508 is performed iteratively until the model loss has stabilized to a defined degree and/or otherwise reached convergence.

Once the cardiotocograph pattern identification model 112 building has progressed to sufficiency on the training data set 504 (e.g., until the model loss has stabilized to a defined degree and/or otherwise reached convergence), the model testing and validation is performed using the validation data set 506. In this regard, the training component 108 can apply the validation set 506 to the model 112 to generate validation results 518, which can be evaluated at 520 to evaluate the performance accuracy and specificity of the model 112. Once the model 112 training (including testing and validation) has been completed, the model 112 can be deployed in actual clinical context to automatically identify and classify patterns in new cardiotocograph data that correspond to defined physiological events and/or conditions.

With reference again to FIG. 1, as noted above, the trained cardiotocograph pattern identification model 112 can be configured to generate a variety of different output data. For example, the output of the model 112 as applied to one input data sample that corresponds to an N minute strip of FHR-UA tracing data (e.g., 10 minutes or another window) can include, but is not limited to: information that identifies any distinct patterns in the data sample that correspond defined physiological events or conditions (e.g., or no pattern if one is not identified), information that classifies that the physiological event or condition that corresponds to each identified pattern (e.g., a FHR acceleration, a FHR deceleration, a region of marked variability, and/or a contraction), information identifying the data in which the pattern was identified (e.g., the FHR data, the UA data, or a combination thereof), and/or information describing/defining attributes or parameters of the identified patterns (e.g., timing attributes, measurement values, amplitude, frequency attributes, spacing attributes, duration attributes, etc.). In some embodiments, the model output information described above can be presented to clinicians as result data in the form of a report and/or in real-time as the new cardiotocograph data is processed by the model 112 in real-time.

Additionally, or alternatively, the post-processing component 114 and/or the analysis component 118 can further process and interpret the model output data to generate more accurate and useful results. To facilitate this end, the post-processing component 114 and the analysis component 118 can employ cardiotocograph interpretation domain knowledge 104 and/or cardiotocograph interpretation schema 116. The cardiotocograph interpretation domain knowledge 104 can include information provided in clinical guidelines, textbooks, articles, and the like that define rules and guidelines for interpreting cardiotocograph data. This information can include aggregated electronic information from various databases and data sources. The cardiotocograph interpretation schema 116 can include similar rules and guidelines for interpreting cardiograph data, yet tailored specifically for system 100 (and other systems described herein), for interpreting the results of the cardiotocograph pattern identification model 112. For example, in some embodiments, the cardiotocograph interpretation schema 116 can defined rules and/or guidelines for removing spurious results by the post-processing component 114. With these embodiments, the post-processing component 114 can be configured to evaluate the identified patterns and their corresponding physiological events based on defined criteria for valid and invalid patterns provided in the cardiotocograph interpretation schema 116, wherein the criteria vary for the different physiological events/condition. For example, the criteria can define thresholds related to timing, duration, frequency, measurement values, and so on. The post-processing component 114 can further remove any identified patterns that fail to pass the defined qualification criteria for the event type from the model results.

The analysis component 118 can also employ the cardiotocograph interpretation domain knowledge 104 and/or the cardiotocograph interpretation schema 116 to further validate whether an identified pattern indicates a corresponding physiological event or condition occurred or not. For example, in some implementations, based on identification of a pattern by the model 112 that correspond to a defined physiological event, the system or analysis component 118 can assume that the event occurred. In other implementations, the analysis component 118 can be configured to perform additional evaluation of the pattern information based on the cardiotocograph interpretation domain knowledge 104 and/or the cardiotocograph interpretation schema 116 to determine with more certainty whether the event or condition did in fact occur. For example, in some implementations, the cardiotocograph interpretation schema 116 can define tailored pattern thresholds for different subjects and clinical contexts based on drugs administered, phase of labor, medical condition of the mother, medical condition of the fetus, medical history of the mother, comorbidities, risk level of the mother, and so on. For instance, fetuses with intrauterine growth restriction are unusually susceptible to the effect of hypoxemia, which tends to progress rapidly, which can cause the thresholds for declaring certain patterns as constituting a hypoxemia related event to be lower in this scenario. Thus, the analysis component 118 can tailor its evaluation of the identified patterns and their correlation to the occurrence of corresponding physiological events or conditions based on other known information about the subject and the clinical context. The analysis component 118 can also aggregate the model output results for sequential input data samples for sequential time segments to generate a timeline of pattern and event information for the subject that spans across a duration of a time. The analysis component 118 can further evaluate the patterns and event information generated by the model longitudinally over time to further clarify the occurrence or non-occurrence of certain events or conditions based on the totality of the aggregated timeline of events and associated patterns.

The analysis component 118 can also employ the cardiotocograph interpretation domain knowledge 104 and/or the cardiotocograph interpretation schema 116 to determine additional information about the physiological state and condition of the mother and/or fetus based on the output of the model 112. For example, in some embodiments, the analysis component 118 can employ defined rules and schema regarding how to interpret the model identified patterns corresponding to defined events/conditions to determine additional parameters associated with the defined physiological events and/or conditions. For example, in some embodiments, the analysis component 118 can determine the baseline FHR based on the regions of FHR variability determined by the model 112 and using one or more defined baseline FHR algorithmic formulas defined in the cardiotocograph interpretation domain knowledge 104 and/or the cardiotocograph interpretation schema 116. Additionally, or alternatively, the model 112 can be configured to predict the baseline FHR based on expert applied ground truth data for the baseline FHR, as shown in FIGS. 3-4. The analysis component 118 can also determine various other parameters related to the identified patterns and corresponding physiological events/conditions, including but not limited to: timing of FHR acceleration, duration of FHR acceleration, degree of FHR acceleration, type of FHR acceleration, timing of FHR deceleration, duration of FHR deceleration, degree of FHR deceleration, type of FHR deceleration, timing of FHR period of variability, duration of fetal heart period of variability, degree of FHR variability, contraction timing, contraction duration, contraction frequency, and contraction type. In some implementations of these embodiments, the cardiotocograph interpretation schema 116 can provide the defined rules, algorithms and/or guidelines used by the analysis component 118 to determine (e.g., calculate) or infer this additional information based on the identified patterns and attributes of the patterns, as well as other input variables related to the patient and the clinical context. The analysis component 118 can also aggregate the model output results for sequential input data samples for sequential time segments to generate a timeline of pattern and event information for the subject that spans across a duration of a time. The analysis component 118 can further summarize the condition and/or status of the mother and/or fetus based on the totality of events and conditions up to the current point of time based on information provided in the cardiotocograph interpretation domain knowledge 104 and/or the cardiotocograph interpretation schema 116.

In some embodiments, the analysis component 118 can employ principles of artificial intelligence to facilitate interpreting the model output data (e.g., the identified patterns and/or their corresponding event classifications) to determine or infer information regarding the clinical condition/state of the mother and/or fetus and/or other relevant parameters associated with the identified patterns and events (e.g., baseline FHR, contraction type, contraction duration, presence of tachysystole, etc.). In certain embodiments, the analysis component 118 can include a prediction component that employs data (e.g., real-time cardiotocograph data, the model output data, the cardiotocograph interpretation schema 116 and/or the cardiotocograph interpretation domain knowledge 104) to monitor a current state of mother and/or fetus. The analysis component 118 can perform interpretation of the cardiotocograph pattern identification model 112 output data explicitly or implicitly. Learning and/or determining inferences by the analysis component 118 can facilitate monitoring of one or more patterns in the patient flow data 118. For example, the analysis component 118 can employ a probabilistic and/or statistical-based analysis (e.g., factoring into the analysis utilities and costs) to interpret the model output data. The analysis component 118 can employ, for example, an SVM classifier to interpret and classify events and/or conditions associated with the identified patterns. Additionally, or alternatively, the analysis component can employ other classification techniques associated with Bayesian networks, decision trees and/or probabilistic classification models. Classifiers employed by the analysis component 119 can be explicitly trained (e.g., via a generic training data) as well as implicitly trained (e.g., via observing user behavior, receiving extrinsic information). For example, with respect to SVM's that are well understood, SVM's are configured via a learning or training phase within a classifier constructor and feature selection module. A classifier is a function that maps an input attribute vector, $x=(x1, x2, x3, x4, xn)$, to a confidence that the input belongs to a class—that is, $f(x)$=confidence(class).

In an aspect, the analysis component 118 can include an inference component that can further enhance automated aspects of the model output interpretation utilizing in part inference-based schemes. The analysis component 118 can employ any suitable machine-learning based techniques, statistical-based techniques and/or probabilistic-based techniques. The analysis component can additionally or alternatively employ a reduced set of factors (e.g., an optimized set of factors) to facilitate providing a most accurate machine learning model for predicting events, conditions and parameters associated with the diagnosis and well-being of the fetus and/or the mother based at least in part on the patterns identified by the cardiotocograph pattern identification model 112. For example, the analysis component 118 can employ expert systems, fuzzy logic, SVMs, HMMs, greedy search algorithms, rule-based systems, Bayesian models (e.g., Bayesian networks), neural networks, other non-linear training techniques, data fusion, utility-based analytical systems, systems employing Bayesian models, etc. In another aspect, the analysis component 118 can perform a set of machine learning computations associated with the one or more patterns in the patient cardiotocograph data identified by the model 112. For example, the analysis component 118 can perform a set of clustering machine learning computations, a set of decision tree machine learning computations, a set of instance-based machine learning computations, a set of regression machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations. The one or more abnormalities parameters, events and/or conditions determined or inferred by the analysis component 118 based at least in part on the output of the model 112 can be reported and stored, for example, in the cardiotocograph interpretation schema 116 and/or the memory 122.

Figure 6:
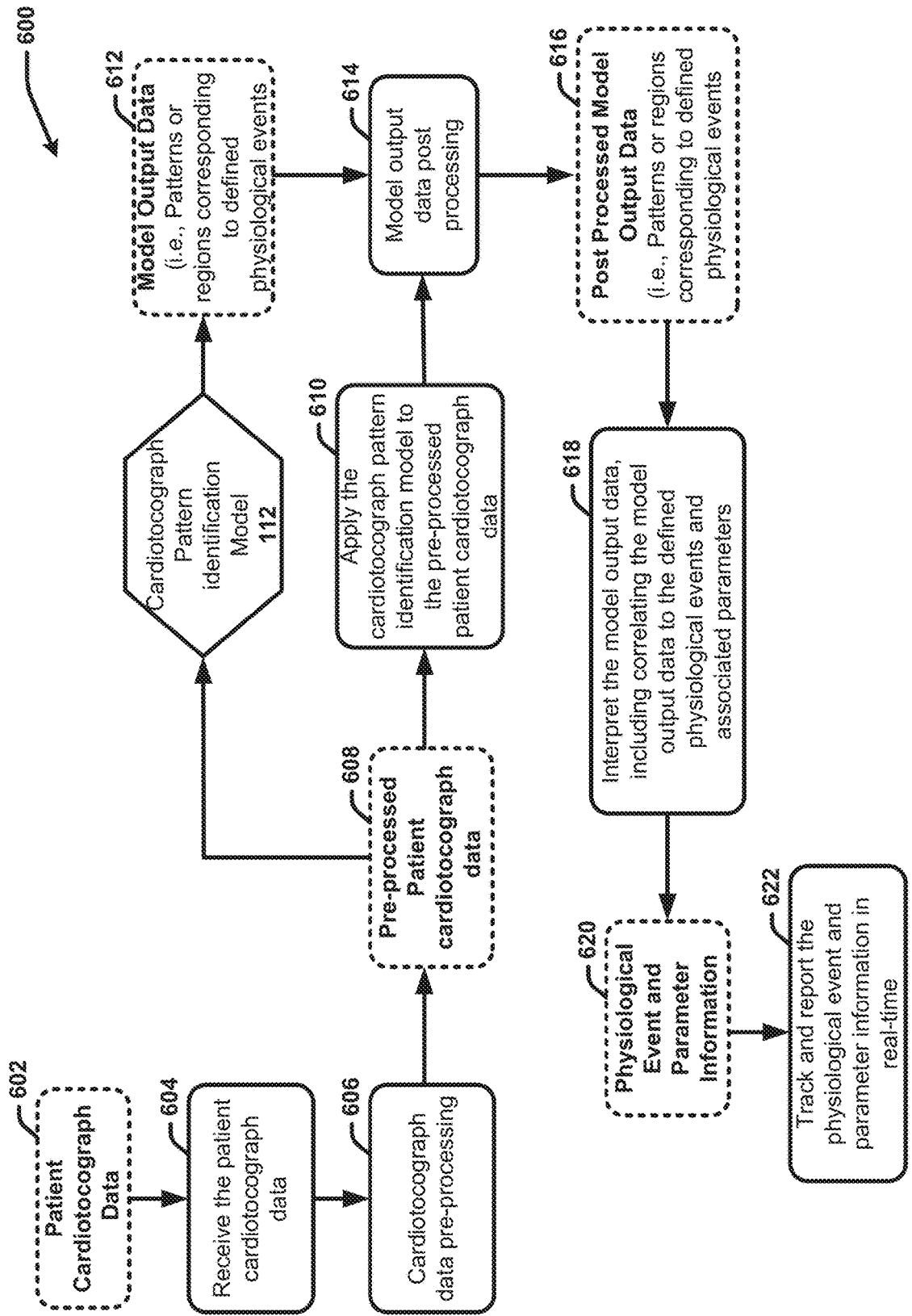
FIG. 6 presents a flow-diagram of an example process for performing FHR-UA analytics in real-time using machine learning techniques in accordance with one or more embodiments of the disclosed subject matter.

FIG. 6 presents a flow-diagram of an example process 600 for performing FHR-UA analytics in real-time using machine learning techniques in accordance with one or more embodiments of the disclosed subject matter. Process 600 provides an example process that can be performed using the cardiotocograph pattern identification model 112 once trained as applied to new cardiotocograph data for a new patient, illustrate in FIG. 6 as patient cardiotocograph data 602. In some implementation, the cardiotocograph data 602 can correspond to a live stream of cardiotocograph data captured for a mother and fetus over a duration of labor. In other implementations, the cardiotocograph data 602 can correspond to a set of previously recorded cardiotocograph data, such as that recorded during a monitoring session. Repetitive description of like elements employed in respective embodiments is omitted for sake of brevity.

In accordance with process 600, at 602, the system can receive the patient cardiotocograph data 602. In implementation in which the patient cardiotocograph data 602 corresponds to real-time FHA-UA tracing data, at 602, this data can be received in real-time. At 606, the system can pre-process the patient cardiotocograph data 602 using one or more pre-processing techniques disclosed herein to generate pre-processed patient cardiotocograph data 608. For example, in some implementations, this can involve segmenting the input data into input data samples that comprise data for defined windows of time (e.g., sequential segments of 10-minute time windows). In some embodiments, the segments can be separated entirely (non-overlapping) back-to-back. For example, a first segment can include times t1-t2, a second segment can include times t2-t3, a third segment can include times t3-t4, and so on. For example, time window t1-t2 can include minutes 0-10, time window t2-23 can include minutes 11-20, time window t3-t4 can include minutes 21-30, and so on. In other embodiments, the segments can be separated in an overlapping fashion. For example, a first segment can include times t1-t2 and correspond to minutes 0-10, a second segment can include times t2-t3 and correspond to minutes 1-11, a third segment can include times t3-t4 and correspond to minutes 2-12 and so on.

At 610, the system can apply the cardiotocograph pattern identification model 112 to the pre-processed patient cardiotocograph data 608 to generate the model output data 612. For example, the model output data 612 can include identified patterns or regions in the input data samples that correspond to defined physiological events. At 614, the system can (optionally) perform post-processing on the model output data (e.g., using post-processing component 114), such as to remove spurious results, convert the output data into another format, or the like. The resulting post-processed model output data is represented in process 600 as post processed model output data 616. At 618, the system can interpret the model output data (e.g., the post-processed model output data 616) using the analysis component 118, the cardiotocograph interpretation schema 116 and/or the cardiotocograph interpretation domain knowledge 104. This can involve for example, correlating the model output data to the defined physiological events and associated parameters (e.g., determining the baseline FHR, determining the contraction duration, determining contraction type, determining tachysystole presence, and so on). The final output of the model 112 and the analysis component 118 processing can include physiological event and parameter information 620 regarding the identified physiological events that have occurred and relevant parameters and associated diagnosis/condition of the mother and/or fetus. At 622, the system can further track and report the physiological event and parameter information, which and be performed in real-time (e.g., over the course of labor) in implementation in which the patient cardiotocograph data 602 is received in real-time.

Figure 7:
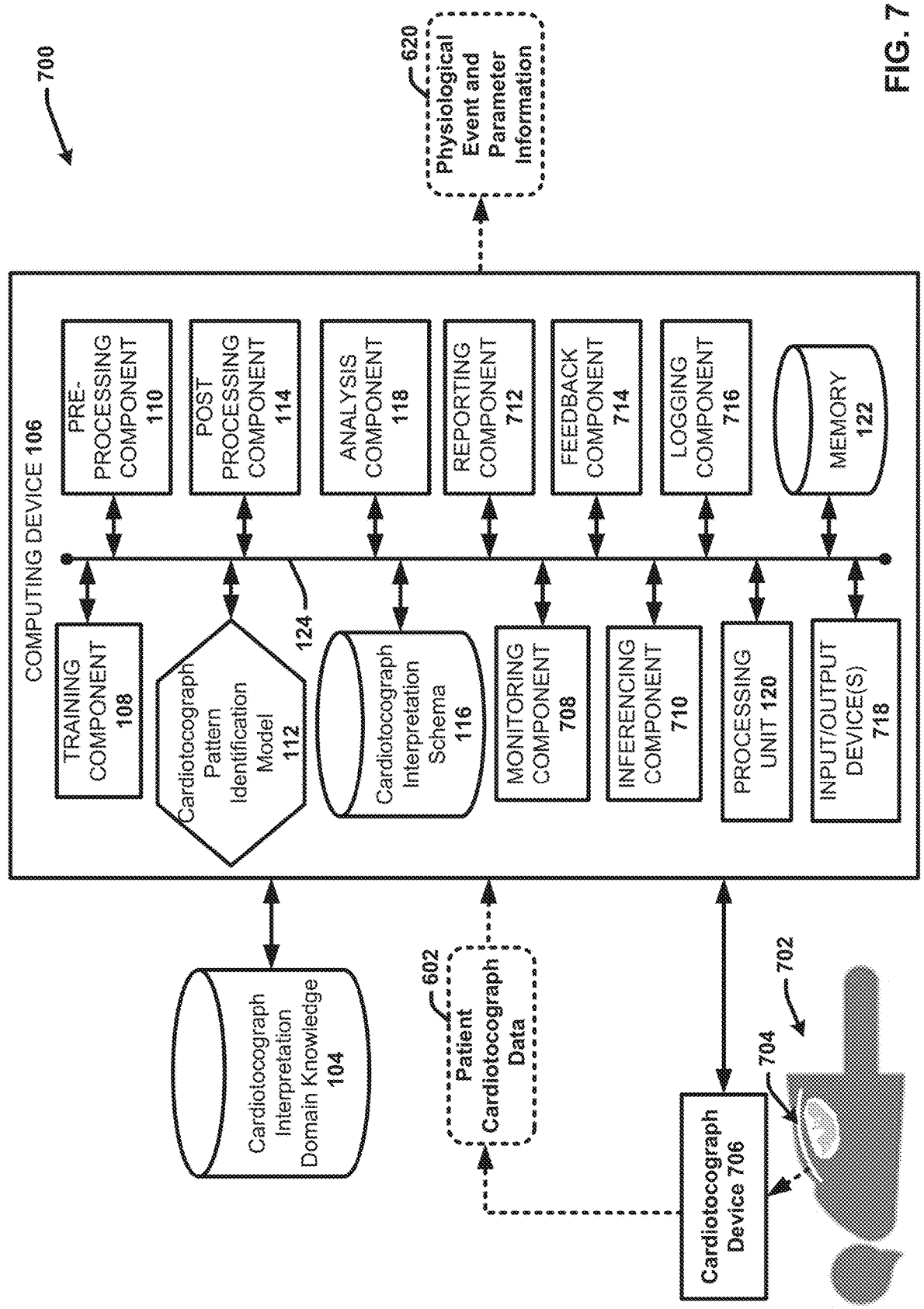
FIG. 7 illustrates an example system for performing FHR-UA analytics in real-time using machine learning techniques in accordance with one or more embodiments of the disclosed subject matter.

FIG. 7 illustrates an example system 700 for performing FHR-UA analytics in real-time using machine learning techniques in accordance with one or more embodiments of the disclosed subject matter. System 700 provides an example system for performing process 600 and similar processes using the one or more trained cardiotocograph pattern identification models 112. System 700 includes same or similar components as system 100 with the addition of monitoring component 708, inferencing component 710, reporting component 712, feedback component 714, logging component 716 and input/output devices 718 to the computing device 106. System 700 further includes a cardiotocograph device 706 that is coupled to a patient 702 and the computing device 106. Repetitive description of like elements employed in respective embodiments is omitted for sake of brevity.

In accordance with system 700, the patient 702 include a mother and fetus. The cardiotocograph device 706 can be electrically and operatively coupled to the patient via one or more sensors 704 (e.g., transducers or the like) that supply FHR and UA reading signals to the cardiotocograph device 706 which convert the signals into time/measurement values and generate the corresponding FHR-UA tracing data for the patient in real-time. The cardiotocograph device 706 further provides the raw signal data and/or the FHR-UA tracing data to the computing device 106 for processing thereof. In the embodiment shown, the raw signal data and/or the FHR-UA tracing data is represented as patient cardiotocograph data 602.

The monitoring component 708 can receive the patient cardiotocograph data 602 from the cardiotocograph device 706. For example, in implementations in which the patient 702 hooked up to the cardiotocograph device 706 over a duration of labor, the monitoring component 706 can receive the patient cardiotocograph data 602 in real-time over the duration of labor. The inferencing component 710 can further apply the cardiotocograph pattern identification model 112 to the patient cardiotocograph data 602 as it is received to generate the model output data (e.g., model output data 612). In this regard, the model output data can include information that identifies patterns in the input data that correspond to defined physiological events associated with the fetus and/or the mother. The analysis component 118 can further determine occurrence of the defined physiological events based on the patterns in the new cardiotocograph data. The analysis component 118 can also determine various other parameters related to the identified patterns and corresponding physiological events/conditions using the cardiotocograph interpretation schema 116 and/or the cardiotocograph interpretation domain knowledge using the techniques described above. For example, this additional information can include, but not limited to: baseline FHR, timing of FHR acceleration, duration of FHR acceleration, degree of FHR acceleration, type of FHR acceleration, timing of FHR deceleration, duration of FHR deceleration, degree of FHR deceleration, type of FHR deceleration, timing of FHR period of variability, duration of fetal heart period of variability, degree of FHR variability, contraction timing, contraction duration, contraction frequency, and contraction type.

The reporting component 712 can further report the results of the model 112 and/or the analysis component 118 in real-time. In this regard, the reporting component 712 can report physiological event and parameter information 620 regarding the identified physiological events that occurred, the related parameters and related diagnosis and condition information to one or more clinicians involved in the treatment of the patient 702 via one or more suitable input/output device 718 (e.g., via display, a speaker, or the like). Some suitable input/output devices are described in FIG. 10 with reference to output device 1036 and input device 1028.

In some embodiments, the feedback component 714 can further facilitate receiving feedback information from the one or more clinicians regarding accuracy of the event information and the parameter information. For example, in some implementations, the reporting component 712 can provide the physiological event and parameter information 620 to the clinicians via an interactive graphical user interface (GUI) that includes a feedback mechanism for receiving user input accepting or rejecting the results. The feedback mechanism can also all the user to provide input identify errors in the results and/or providing corrections to the results. The logging component 716 can further log the feedback information with the new cardiograph data recorded for the patient 602 in an indexed data structure, wherein the training component 106 further employs the feedback information in association with retraining and refining the cardiotocograph pattern identification model 112 over time (e.g., offline).

As described herein, a real-time computer system can be defined a computer system that performs its functions and responds to external, asynchronous events within a defined, predictable (or deterministic) amount of time. A real-time computer system such as system 700 typically controls a process (e.g., monitoring patient cardiotocograph data 602 and, identifying patterns in the data corresponding to physiological events and conditions, and reporting the data) by recognizing and responding to discrete events within predictable time intervals, and by processing and storing large amounts of data acquired from the controlled system (e.g., the cardiotocograph device 706). Response time and data throughput requirements can depend on the specific real-time application, data acquisition and critical nature of the type of decision support provided. In the regard, the term "real-time" as used herein with reference to processing and generating information by computing device 106 refers to performance of these actions within a defined or predictable amount of time (e.g., a few seconds, less than 10 seconds, less than a minute, etc.) between reception of the patient cardiotocograph data 602 by the monitoring component 708.

The deployment architecture of system 700 (and other systems described herein) can vary. In some embodiments, the components of the computing device 106 can be deployed at and executed by a single computing device (e.g., real or virtual) operatively coupled to the processing unit 120 and the memory 122. In some implementations of these embodiments, the computing device 106 and the cardiotocograph device 706 may be physically, operatively, and/or communicatively coupled. In other embodiments, one or more components of computing device 106 can be deployed at two or more separate communicatively coupled computing devices operating in a distributed computing environment. The separate computing devices can be communicatively coupled via one or more wired or wireless communication networks. Various alternative deployment architecture variations can also be used.

Figure 8:
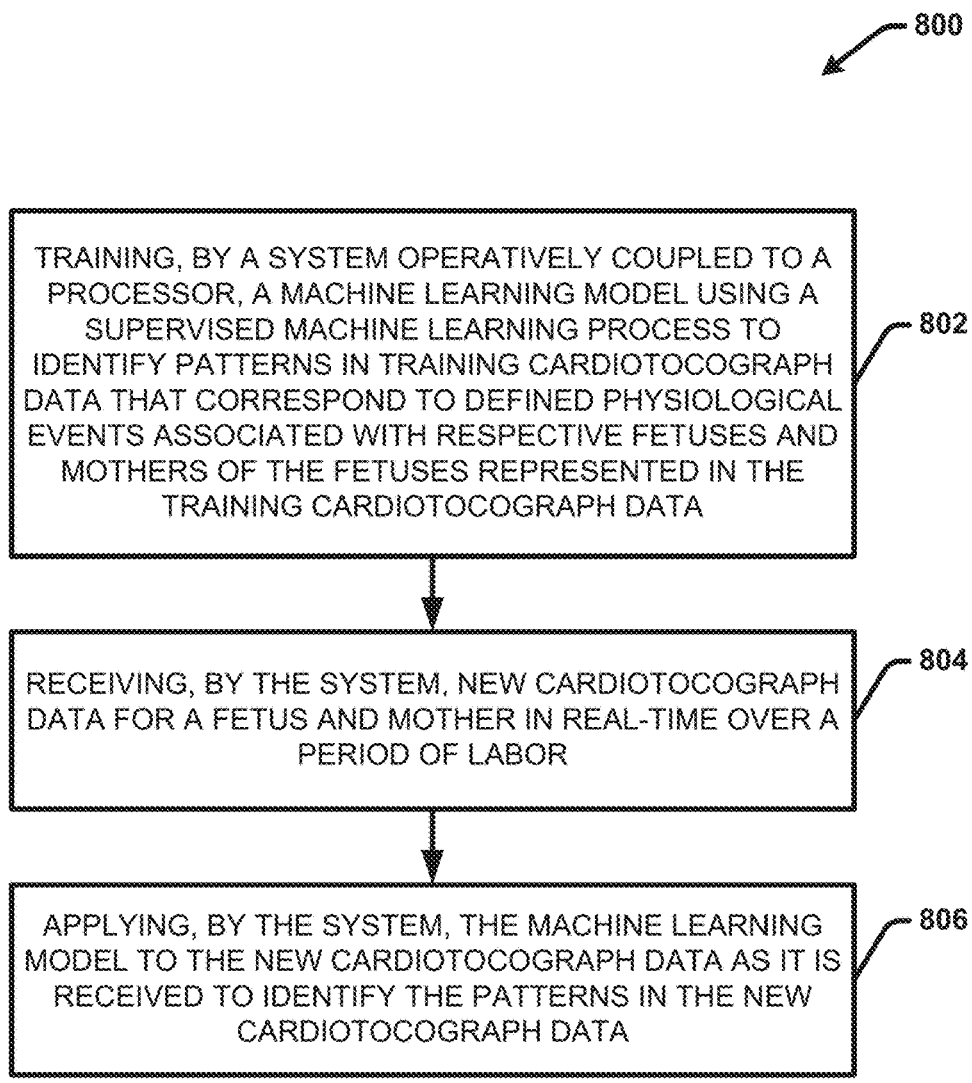
FIG. 8 presents a high-level flow diagram of an example computer-implemented process performing FHR analytics using machine learning techniques in accordance with one or more embodiments of the disclosed subject matter.

FIG. 8 presents a high-level flow diagram of an example computer-implemented process 800 performing FHR analytics using machine learning techniques in accordance with one or more embodiments of the disclosed subject matter. Repetitive description of like elements employed in respective embodiments is omitted for sake of brevity.

In accordance with process 800, at 802 a system operatively coupled to a processor (e.g., system 100, system 700 and the like) trains (e.g., using training component 108) a machine learning model (e.g., cardiotocograph pattern identification model 112) using a supervised machine learning process (e.g., process 500 or the like) to identify patterns in training cardiotocograph data (e.g., cardiotocograph training data 102) that correspond to defined physiological events associated with respective fetuses and mothers of the fetuses represented in the training cardiotocograph data. For example, the patterns can correspond to a FHR acceleration, a FHR deceleration, a uterine contraction, a period of FHR variability, and a uterine tachysystole. Other physiological events that may be reflected by defined patterns in the cardiotocograph data are also envisioned. Once the model training has been completed, at 804, the system can receive new cardiotocograph data for a fetus and mother (e.g., patient cardiotocograph data 602) in real-time over a period of labor (e.g., via monitoring component 708). At 806, the system can apply (e.g., via inferencing component 710) the machine learning model to the new cardiotocograph data as it is received to identify the patterns in the new cardiotocograph data.

Figure 9:
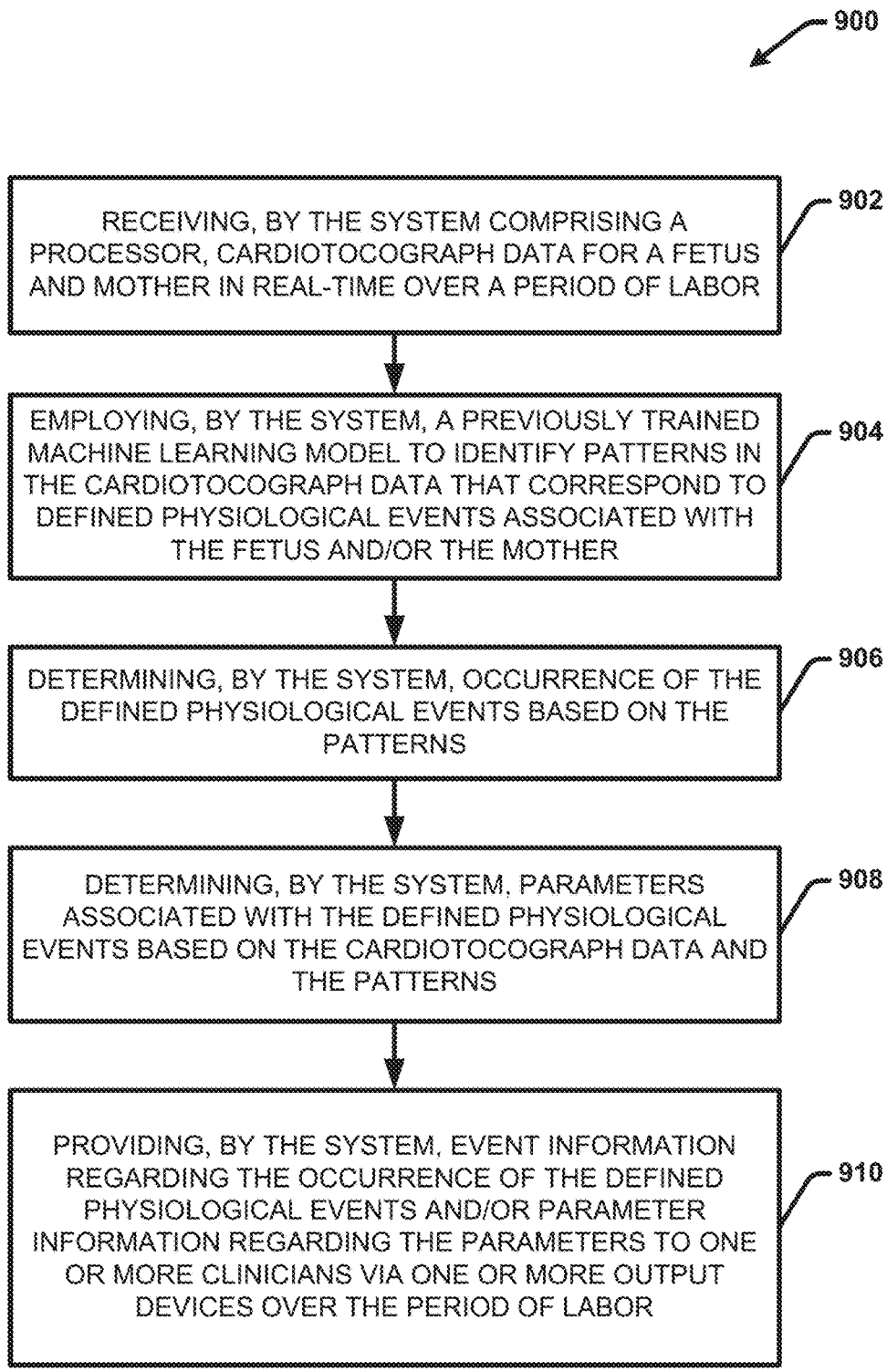
FIG. 9 presents a high-level flow diagram of another example computer-implemented process performing FHR analytics using machine learning techniques in accordance with one or more embodiments of the disclosed subject matter.

FIG. 9 presents a high-level flow diagram of another example computer-implemented process 900 performing FHR analytics using machine learning techniques in accordance with one or more embodiments of the disclosed subject matter. Repetitive description of like elements employed in respective embodiments is omitted for sake of brevity.

In accordance with process 900, at 902 a system operatively coupled to a processor (e.g., system 700 and the like) receives cardiotocograph data for a fetus and mother (e.g., patient cardiotocograph data 602) in real-time over a period of labor (e.g., via monitoring component 708). At 904, the system employs a previously trained machine learning model (e.g., cardiotocograph pattern identification model 112) to identify patterns in the cardiotocograph data that correspond to defined physiological events associated with the fetus and/or the mother (e.g., via inferencing component 710). At 906, the system determines occurrence of the defined physiological events based on the patterns (e.g., via inferencing component 710 and/or analysis component 118). For example, in some embodiments, the cardiotocograph pattern identification model 112 can be configured to directly correlate a pattern in the cardiotocograph data to one or more defined physiological events, such as a FHR acceleration, a FHR deceleration, a period of FHR variability or a contraction. In some implementations of these embodiments, in response to detection of a pattern that corresponds to such an event, the inferencing component 710 can generate an output that indicates that event occurred and the timing of occurrence. Additionally, or alternatively, the analysis component 118 can further analyze the detected patterns in view of cardiotocograph interpretation schema 116 and using one or more additional machine learning and/or rule-based algorithms to facilitate correlating the detected patterns to occurrence of the defined physiological events.

At 908, the system determines parameters associated with the defined physiological events based on the cardiotocograph data and the patterns (e.g., via analysis component 118 and using cardiotocograph interpretation schema 116). For example, the parameters may include, but are not limited to: baseline FHR, timing of FHR acceleration, duration of FHR acceleration, degree of FHR acceleration, type of FHR acceleration, timing of FHR deceleration, duration of FHR deceleration, degree of FHR deceleration, type of FHR deceleration, timing of FHR period of variability, duration of fetal heart period of variability, degree of FHR variability, contraction timing, contraction duration, contraction frequency, and contraction type. At 910, the system provides (e.g., via reporting component 712) event information regarding the occurrence of the defined physiological events and/or parameter information regarding the parameters (e.g., physiological event and parameter information 620) to one or more clinicians via one or more output devices (e.g., via a display monitor, a speaker, or the like) over the period of labor.

Example Operating Environment

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, procedural programming languages, such as the "C" programming language or similar programming languages, and machine-learning programming languages such as like CUDA, Python, Tensorflow, PyTorch, and the like. The computer readable program instructions can execute entirely on the user's computer, partly on the user's computer, as a stand-alone software package, partly on the user's computer and partly on a remote computer or entirely on the remote computer or server using suitable processing hardware. In the latter scenario, the remote computer can be connected to the user's computer through any type of network, including a local area network (LAN) or a wide area network (WAN), or the connection can be made to an external computer (for example, through the Internet using an Internet Service Provider). In various embodiments involving machine-learning programming instructions, the processing hardware can include one or more graphics processing units (GPUs), central processing units (CPUs), and the like. For example, one or more of the disclosed machine-learning models (e.g., the cardiotocograph pattern identification model 112) may be written in a suitable machine-learning programming language and executed via one or more GPUs, CPUs or combinations thereof. In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 10, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 10:
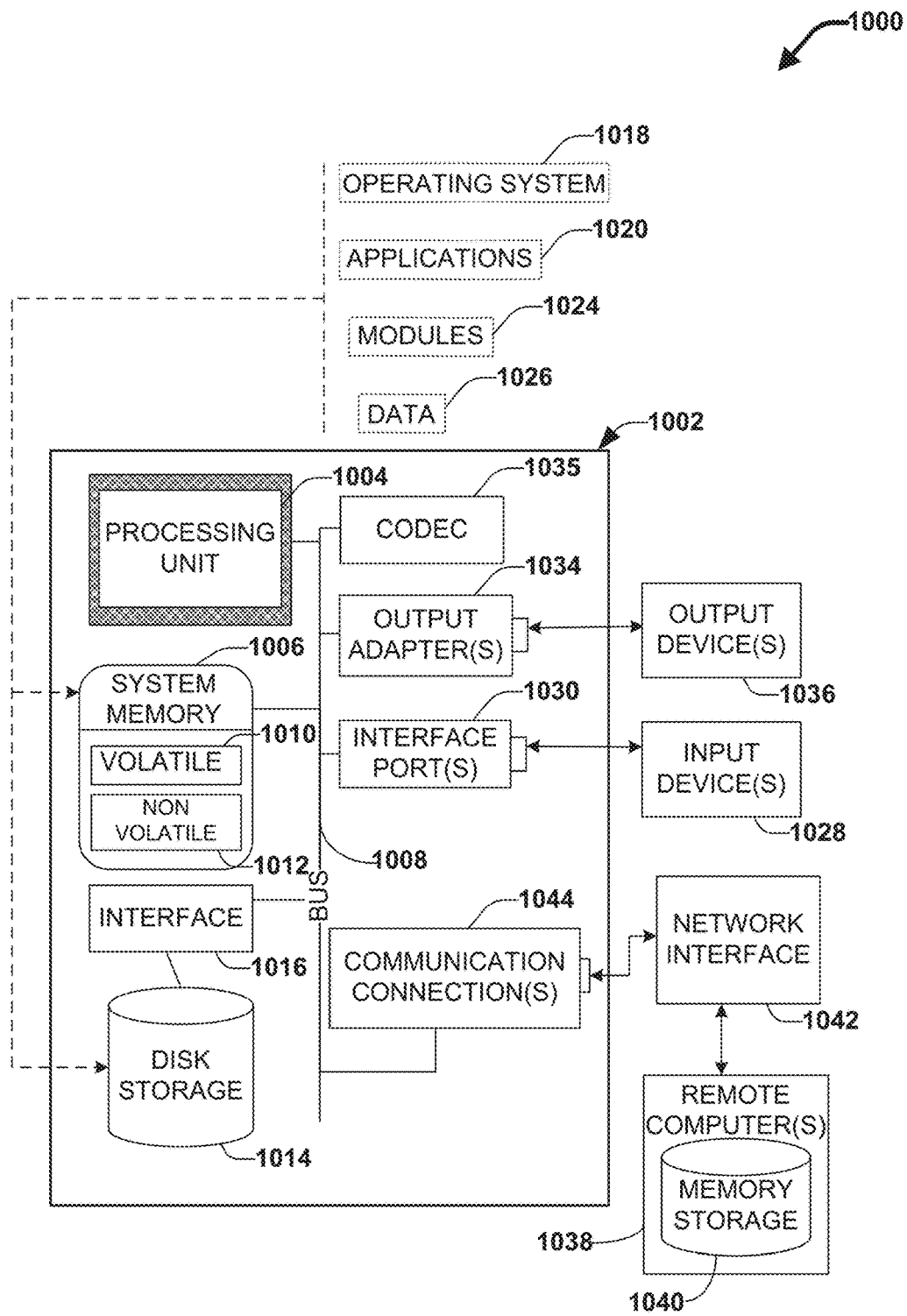
FIG. 10 illustrates a block diagram of an example, non-limiting operating environment in which one or more embodiments described herein can be facilitated.

With reference to FIG. 10, an example environment 1000 for implementing various aspects of the claimed subject matter includes a computer 1002. The computer 1002 includes a processing unit 1004, a system memory 1006, a codec 1035, and a system bus 1008. The system bus 1008 couples system components including, but not limited to, the system memory 1006 to the processing unit 1004. The processing unit 1004 can be any of various available processors. Dual microprocessors, one or more GPUs, CPUs, and other multiprocessor architectures also can be employed as the processing unit 1004.

The system bus 1008 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1006 includes volatile memory 1026 and non-volatile memory 1012, which can employ one or more of the disclosed memory architectures, in various embodiments. The basic input/output system (BIOS), containing the basic routines to transfer information between elements within the computer 1002, such as during start-up, is stored in non-volatile memory 1012. In addition, according to present innovations, codec 1035 can include at least one of an encoder or decoder, wherein the at least one of an encoder or decoder can consist of hardware, software, or a combination of hardware and software. Although, codec 1035 is depicted as a separate component, codec 1035 can be contained within non-volatile memory 1012. By way of illustration, and not limitation, non-volatile memory 1012 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1012 can employ one or more of the disclosed memory devices, in at least some embodiments. Moreover, non-volatile memory 1012 can be computer memory (e.g., physically integrated with computer 1002 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1026 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1002 can also include removable/non-removable, volatile/non-volatile computer storage medium. FIG. 10 illustrates, for example, disk storage 1014. Disk storage 1014 includes, but is not limited to, devices like a magnetic disk drive, solid state disk (SSD), flash memory card, or memory stick. In addition, disk storage 1014 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1014 to the system bus 1008, a removable or non-removable interface is typically used, such as interface 1016. It is appreciated that disk storage 1014 can store information related to a user. Such information might be stored at or provided to a server or to an application running on a user device. In one embodiment, the user can be notified (e.g., by way of output device(s) 1036) of the types of information that are stored to disk storage 1014 or transmitted to the server or application. The user can be provided the opportunity to opt-in or opt-out of having such information collected or shared with the server or application (e.g., by way of input from input device(s) 1028).

It is to be appreciated that FIG. 10 describes software that acts as an intermediary between users and the basic computer resources described in the suitable operating environment 1000. Such software includes an operating system 1018. Operating system 1018, which can be stored on disk storage 1014, acts to control and allocate resources of the computer 1002. Applications 1020 take advantage of the management of resources by operating system 1018 through program modules 1024, and program data 1010, such as the boot/shutdown transaction table and the like, stored either in system memory 1006 or on disk storage 1014. It is to be appreciated that the claimed subject matter can be implemented with various operating systems or combinations of operating systems.

A user enters commands or information into the computer 1002 through input device(s) 1028. Input devices 1028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1004 through the system bus 1008 via interface port(s) 1030. Interface port(s) 1030 include, for example, a serial port, a parallel port, a game port, and a universal serial bus (USB). Output device(s) 1036 use some of the same type of ports as input device(s) 1028. Thus, for example, a USB port can be used to provide input to computer 1002 and to output information from computer 1002 to an output device 1036. Output adapter 1034 is provided to illustrate that there are some output devices 1036 like monitors, speakers, and printers, among other output devices 1036, which require special adapters. The output adapters 1034 include, by way of illustration and not limitation, video and sound cards that provide a means of connection between the output device 1036 and the system bus 1008. It should be noted that other devices or systems of devices provide both input and output capabilities such as remote computer(s) 1038.

Computer 1002 can operate in a networked environment using logical connections to one or more remote computers, such as remote computer(s) 1038. The remote computer(s) 1038 can be a personal computer, a server, a router, a network PC, a workstation, a microprocessor based appliance, a peer device, a smart phone, a tablet, or other network node, and typically includes many of the elements described relative to computer 1002. For purposes of brevity, only a memory storage device 1040 is illustrated with remote computer(s) 1038. Remote computer(s) 1038 is logically connected to computer 1002 through a network interface 1042 and then connected via communication connection(s) 1044. Network interface 1042 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1044 refers to the hardware/software employed to connect the network interface 1042 to the bus 1008. While communication connection 1044 is shown for illustrative clarity inside computer 1002, it can also be external to computer 1002. The hardware/software necessary for connection to the network interface 1042 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
    a memory that stores computer executable components; and
    a processor that executes the computer executable components stored in the memory to perform operations comprising:
        train a machine learning model, using training cardiotocograph data associated with fetuses and mothers of the fetuses, to identify graphical patterns in cardiotocograph graphical tracings of the training cardiotocograph data corresponding to defined physiological events associated with hearts of the fetuses and uteruses of the mothers of the fetuses during labor;
        train the machine learning model, using timeline information associated with the graphical patterns and the defined physiological events, to:
            identify longitudinal correlations amongst at least two of the graphical patterns in different time periods, and
            determine, based on the longitudinal correlations, whether the defined physiological events respectively actually occurred;
        continuously analyze, in real-time during labor of a mother of a fetus, using the machine learning model, cardiotocograph data for the fetus and the mother of the fetus;
        identify, in real-time during the labor, using the machine learning model based on the analysis, a graphical pattern in a cardiotocograph graphical tracing of the cardiotocograph data corresponding to a defined physiological event of the defined physiological events;
        determine, in real-time during the labor, using the machine learning model based on an identified correlation to at least one of a previously identified graphical pattern or a subsequently identified graphical pattern in the cardiotocograph graphical tracing, whether the defined physiological event actually occurred; and
        in response to determining, in real-time during the labor, using the machine learning model, that the defined physiological event actually occurred:
            generate, in real-time during the labor, using the machine learning model, based on the analysis, a group of parameter values derived from the graphical pattern for parameters used in diagnosing one or more conditions of at least one of the mother or the fetus associated with the defined physiological event; and
            provide, in real-time during the labor, a report indicating the defined physiological event and the group of parameter values for the parameters to a device associated with a clinician treating the mother during the labor.

2. The system of claim 1, wherein at least some of the training cardiotocograph data comprises annotated cardiotocograph data annotated with information identifying the graphical patterns and the defined physiological events that respectively correspond to the graphical patterns, and wherein the training comprises employing the annotated cardiotocograph data as ground truth.

3. The system of claim 2, wherein the annotated cardiotocograph data comprises annotations applied to the cardiotocograph graphical tracings.

4. The system of claim 3, wherein the operations further comprise:
    convert the annotated cardiotocograph data into a machine-readable format for processing by the machine learning model.

5. The system of claim 1, wherein the operations further comprise:
    receive feedback information from the clinician regarding accuracy of the defined physiological event and the group of parameter values for the parameters; and retrain the machine learning model based on the feedback information regarding the accuracy of the defined physiological event and the group of parameter values for the parameters.

6. The system of claim 1, wherein the defined physiological events are selected from a group consisting of: a fetal heart rate acceleration, a fetal heart rate deceleration, a uterine contraction, a period of fetal heart rate variability, and a uterine tachysystole.

7. The system of claim 1, wherein the parameters are selected from a group consisting of: baseline fetal heart rate, timing of fetal heart rate acceleration, duration of fetal heart rate acceleration, degree of fetal heart rate acceleration, type of fetal heart rate acceleration, timing of fetal heart rate deceleration, duration of fetal heart rate deceleration, degree of fetal heart rate deceleration, type of fetal heart rate deceleration, timing of fetal heart rate period of variability, duration of fetal heart period of variability, degree of fetal heart rate variability, contraction timing, contraction duration, contraction frequency, and contraction type.

8. A method, comprising:
training, by a system operatively coupled to a processor, a machine learning model using training cardiotocograph data associated with fetuses and mothers of the fetuses, to identify graphical patterns in cardiotocograph graphical tracings of the training cardiotocograph data corresponding to defined physiological events associated with hearts of the fetuses and uteruses of the mothers of the fetuses during labor;
training, by the system, the machine learning model, using timeline information associated with the graphical patterns and the defined physiological events, to:
identify longitudinal correlations amongst at least two of the graphical patterns in different time periods, and
determine, based on the longitudinal correlations, whether the defined physiological events respectively actually occurred;
continuously analyzing, by the system, in real-time during labor of a mother of a fetus, using the machine learning model, cardiotocograph data for the fetus and the mother of the fetus; and
identifying, by the system, in real-time during the labor, using the machine learning model based on the analysis, a graphical pattern in a cardiotocograph graphical tracing of the cardiotocograph data corresponding to a defined physiological event of the defined physiological events;
determining, by the system, in real-time during the labor, using the machine learning model based on an identified correlation to at least one of a previously identified graphical pattern or a subsequently identified graphical pattern in the cardiotocograph graphical tracing, whether the defined physiological event actually occurred; and
in response to determining, in real-time during the labor, using the machine learning model, that the defined physiological event actually occurred:
generating, by the system, in real-time during the labor, using the machine learning model, based on the analysis, a group of parameter values derived from the graphical pattern for parameters used in diagnosing one or more conditions of at least one of the mother or the fetus associated with the defined physiological event; and
providing, by the system, in real-time during the labor, a report indicating the defined physiological event and the group of parameter values for the parameters to a device associated with a clinician treating the mother during the labor.

9. The method of claim 8, wherein at least some of the training cardiotocograph data comprises annotated cardiotocograph data annotated with information identifying the graphical patterns and the defined physiological events that respectively correspond to the graphical patterns, and wherein the training comprises employing the annotated cardiotocograph data as ground truth.

10. The method of claim 9, wherein the annotated cardiotocograph data comprises annotations applied to the cardiotocograph graphical tracings.

11. The method of claim 10, further comprising:
converting, by the system, the annotated cardiotocograph data into a machine-readable format for processing by the machine learning model.

12. The method of claim 8, wherein the defined physiological events are selected from a group consisting of: a fetal heart rate acceleration, a fetal heart rate deceleration, a uterine contraction, a period of fetal heart rate variability, and a uterine tachysystole.

13. The method of claim 8, wherein the parameters are selected from a group consisting of: baseline fetal heart rate, timing of fetal heart rate acceleration, duration of fetal heart rate acceleration, degree of fetal heart rate acceleration, type of fetal heart rate acceleration, timing of fetal heart rate deceleration, duration of fetal heart rate deceleration, degree of fetal heart rate deceleration, type of fetal heart rate deceleration, timing of fetal heart rate period of variability, duration of fetal heart period of variability, degree of fetal heart rate variability, contraction timing, contraction duration, contraction frequency, and contraction type.

14. The method of claim 8, further comprising:
receiving, by the system, feedback information from the clinician regarding accuracy of the defined physiological event and the group of parameter values for the parameters;
retraining, by the system, the machine learning model based on the feedback information regarding the accuracy of the defined physiological event and the group of parameter values for the parameters.

15. A non-transitory machine-readable medium, comprising executable instructions that, when executed by a processor, facilitate performance of operations, comprising:
training a machine learning model using training cardiotocograph data associated with fetuses and mothers of the fetuses, to identify graphical patterns in cardiotocograph graphical tracings of the training cardiotocograph data corresponding to defined physiological events associated with hearts of the fetuses and uteruses of the mothers of the fetuses during labor;
training the machine learning model, using timeline information associated with the graphical patterns and the defined physiological events, to:
identify longitudinal correlations amongst at least two of the graphical patterns in different time periods, and
determine, based on the longitudinal correlations, whether the defined physiological events respectively actually occurred;
continuously analyzing, in real-time during labor of a mother of a fetus, using the machine learning model, cardiotocograph data for the fetus and the mother of the fetus; and
identifying, in real-time during the labor, using the machine learning model based on the analysis, a graphical pattern in a cardiotocograph graphical tracing of the cardiotocograph data corresponding to a defined physiological event of the defined physiological events;

determining, in real-time during the labor, using the machine learning model based on an identified correlation to at least one of a previously identified graphical pattern or a subsequently identified graphical pattern in the cardiotocograph graphical tracing, whether the defined physiological event actually occurred; and in response to determining, in real-time during the labor, using the machine learning model, that the defined physiological event actually occurred:

generating, in real-time during the labor, using the machine learning model, based on the analysis, a group of parameter values derived from the graphical pattern for parameters used in diagnosing one or more conditions of at least one of the mother or the fetus associated with the defined physiological event; and providing, in real-time during the labor, a report indicating the defined physiological event and the group of parameter values for the parameters to a device associated with a clinician treating the mother during the labor.

16. The non-transitory machine-readable medium of claim 15, wherein at least some of the training cardiotocograph data comprises annotated cardiotocograph data annotated with information identifying the graphical patterns and the defined physiological events that respectively correspond to the graphical patterns, and wherein the training comprises employing the annotated cardiotocograph data as ground truth.

17. The non-transitory machine-readable medium of claim 15, wherein the defined physiological events are selected from a group consisting of: a fetal heart rate acceleration, a fetal heart rate deceleration, a uterine contraction, a period of fetal heart rate variability, and a uterine tachysystole.

18. The non-transitory machine-readable medium of claim 15, wherein the parameters are selected from a group consisting of: baseline fetal heart rate, timing of fetal heart rate acceleration, duration of fetal heart rate acceleration, degree of fetal heart rate acceleration, type of fetal heart rate acceleration, timing of fetal heart rate deceleration, duration of fetal heart rate deceleration, degree of fetal heart rate deceleration, type of fetal heart rate deceleration, timing of fetal heart rate period of variability, duration of fetal heart period of variability, degree of fetal heart rate variability, contraction timing, contraction duration, contraction frequency, and contraction type.

19. The non-transitory machine-readable medium of claim 15, the operations further comprising:

receiving feedback information from the clinician regarding accuracy of the defined physiological event and the group of parameter values for the parameters;

retraining the machine learning model based on the feedback information regarding the accuracy of the defined physiological event and the group of parameter values for the parameters.

* * * * *